US005320942A

United States Patent [19]
Quaranta et al.

[11] Patent Number: 5,320,942
[45] Date of Patent: Jun. 14, 1994

[54] METHOD OF DIAGNOSING THE PRESENCE OF ABNORMAL EPITHELIAL TISSUE USING MONOCLONAL ANTIBODIES TO THE A$_6$B$_4$ CELL SURFACE PROTEIN

[76] Inventors: Vito Quaranta, 8861 Nottingham Pl., La Jolla, Calif. 92037; Shama Kajiji, 104 Mistuxet Ave., Mystic, Conn. 06355

[21] Appl. No.: 591,105

[22] Filed: Oct. 1, 1990

Related U.S. Application Data

[63] Continuation-in-part of Ser. No. 293,384, Jan. 4, 1989, abandoned, which is a continuation-in-part of Ser. No. 16,552, Feb. 19, 1987, abandoned.

[51] Int. Cl.$^5$ .................. C12Q 1/04; C07K 15/28
[52] U.S. Cl. .................. 435/7.23; 530/388.2; 530/388.8; 530/388.85
[58] Field of Search .................. 435/7.1, 7.2, 7.21, 435/7.23; 436/501, 503; 530/388.2, 388.22, 388.8, 388.85, 389.7, 391.3, 395

[56] References Cited

U.S. PATENT DOCUMENTS

| | | | |
|---|---|---|---|
| 4,444,744 | 4/1984 | Goldenberg | 424/1.1 |
| 4,485,093 | 11/1984 | Runge | 424/85.91 |
| 4,664,911 | 5/1987 | Uhr et al. | 424/85.91 |

FOREIGN PATENT DOCUMENTS

0154550A3 9/1985 European Pat. Off. .
3329184A1 2/1985 Fed. Rep. of Germany .

OTHER PUBLICATIONS

Akijima, et al., *Chemical Abstracts*, 106:526, Ab. 100759e (1987).
Brown, et al., *Cell*, 59:185–195 (1989).
Burnside, et al., *J. Cell Biology*, 105:397–402 (1987).
Cheresh, et al., *Cell*, 57:59–69 (1989).
Drewinko, et al., *Cancer Res.*, 36:467–475 (1976).
Falcioni, et al., *Cancer Res.*, 46:5772–5778 (1986).
Falcioni, et al., *Cancer Res.*, 48:816–821 (1988).
Freed, et al., *Embo J.*, 8:2955–2965 (1989).
Hemler, et al., *J. Biol. Chem.*, 264:6529–6535 (1989).
Hogervorst, et al., *Embo J.*, 9:765–770 (1990).
Holzmann, et al., *Cell*, 56:37–46 (1989).
Kajiji, et al., *Cancer Res.*, 47:1367–1376 (1987).
Kajiji, et al., *Embo J.*, 8:673–680 (1989).
Kennel, et al., *Cancer Res.*, 41: 3465–3470 (1981).
Kennel, et al., *Cancer Res.*, 46:707–712 (1986).
Kohler, et al., *Nature*, 256:495–497 (1975).
Leptin, et al., *Embo J.*, 6: 1037–1043 (1987).
Maimonis, et al., *Hybridoma*, 4: 77 (1985).
Metzgar, et al., *Cancer Res.*, 42:601–608 (1982).
Miller, et al., *J. Immunol.*, 138:2381–2383 (1987).
Poncz, et al., *J. Biol. Chem.*, 262:8476–8482 (1987).
Ruoslahti, et al., *Cancer Cells*, 1:119–126 (1989).
Schmiegel, et al., *Cancer Res.*, 45:1402–1407 (1985).
Sheppard, et al., *J. Biol. Chem.*, 265:11502–11507 (1990).
Sonnenberg, et al., *J. Histochem. Cytochem*, 34:1037–1046 (1986).
Sonnenberg, et al., *Nature*, 336:487–489 (1988).
Springer, et al., *Nature*, 314:540–542 (1985).
Suzuki, et al., *Embo J.*, 9:757–763 (1990).
Suzuki, et al., *Proc. Natl. Acad. Sci. USA*, 83:8614–8618 (1986).
Takada, et al., *J. Cell Biol.*, 109:397–407 (1989).
Takada, et al., *Proc. Natl. Acad. Sci. USA*, 84:3239–3243 (1987).
Usui, et al., *Sapporo Medical J.*, 54(2): 155–166 (1985).
Kennel et al., "Analysis of the Tumor-Associated Antigen TSP-180: Identity with L$^6$B$^4$ in the Integrin Superfamily," *J. Biol. Chem.* 264 (26):15515–15521, Sep. 15, 1989.
Valenzuela et al., "Tissue Immunofluorescence," in *The Manual of Clinical Laboratory Immunology*, Rose et al., eds. American Society for Microbiology, 1986.

*Primary Examiner*—Y. Christina Chan
*Assistant Examiner*—Robert D. Budens
*Attorney, Agent, or Firm*—Douglas A. Bingham; Thomas Fitting; April C. Logan

[57] ABSTRACT

The present invention discloses a novel cell surface marker and antigenic portions thereof; antibodies reactive with said marker; polynucleotides encoding said marker and antigenic portions thereof; methods of diagnosis and treatment using said polynucleotides and antibodies.

2 Claims, 19 Drawing Sheets

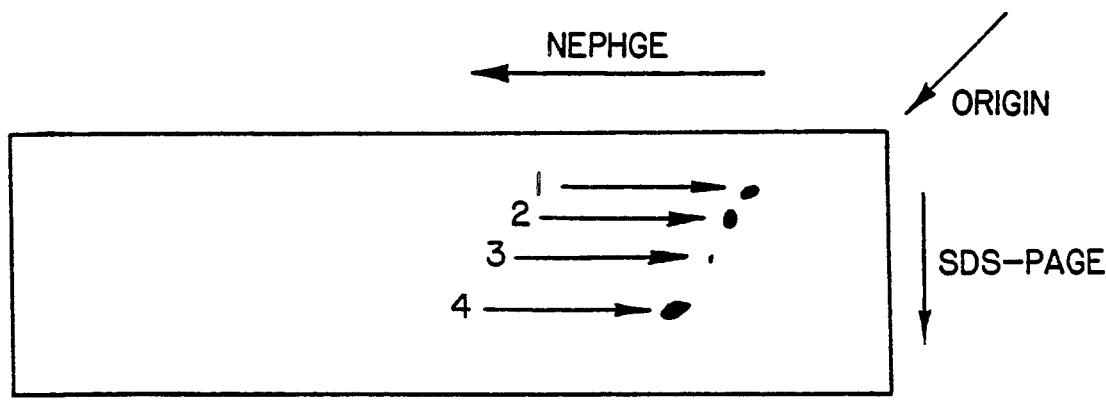
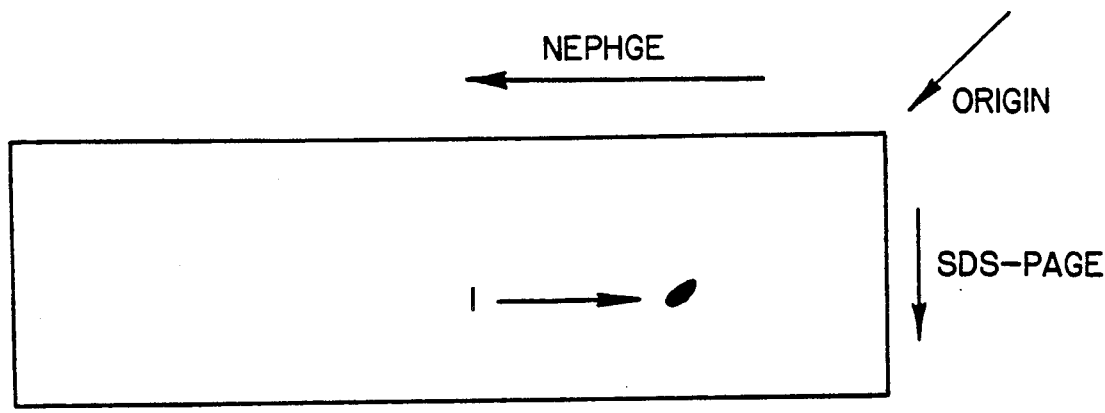

FIG.6A

```
   1 GCGGACCGTCCCGGGGTGGGGCCGGGCCAGCGGGCAGCGGGAGCGGCGAAGGTGGCTGCGGTAGCAGCAGCGCGGCAGCCTCGGACCCAGCCCGGAGCGC        18
 101 AGGGCGGGCCCGCTGCAGGTCCCCGCTCCCCTCCCCCCGTCTCCGCCATGGCTGCCGCGGGCCAGCTGTGCTTGCTCTACCTGTCGGCGGGGCTCCTGTCC        52
                                          M  A  A  A  G  Q  L  C  L  L  Y  L  S  A  G  L  L  S
 201 CGGCTCGGCGCAGCCTTCAACTTGGACACTCGGGAGGACAACGTGATCCGGAAATATGGAGACCCCGGAGCCCTCTTCGGCTTCTCGCTGGCCATGCACT        85
       R  L  G  A  A  F  N  L  D  T  R  E  D  N  V  I  R  K  Y  G  D  P  G  S  L  F  G  F  S  L  A  M  H  W
 301 GGCAACTGCAGCCGGAGGACAAGCGGCTTCTGTTGGTTGCTGGCCCTCGCGGGGAGGCCTTCCACTGCAGAGAGCTTGATAACGATGCTGACCCCACGTG       118
       Q  L  Q  P  E  D  K  R  L  L  L  V  G  A  P  R  G  E  A  L  P  L  Q  R  A  F  R  T  G  G  L  Y  S
 401 CTGCGACATCACCGCCCGCGGGGCCATGCAAGGTCGTGACATGTGCTCACCGATATGAAAAAAAGGCAGCATGTTAATACGAAGCAGGAATCCCGAGACATCTTTG       152
       C  D  I  T  A  R  G  P  C  T  R  I  E  F  D  N  D  A  D  P  T  S  E  S  K  E  D  Q  W  M  G  V  T
 501 GTCCAGAGCCAAGGTCCAGGGGGCAAGGTCGTTACAGAATCTCAGGATTGAAGACGATATGGGGGAGATTGAGAGGCCATGAGAGAATT       185
       V  Q  S  Q  G  P  G  G  K  V  V  T  C  A  H  R  Y  E  K  R  Q  H  V  N  T  K  Q  E  S  R  D  I  F  G
 601 GGCGGTGTTATGTCCTGAGTCAGAATCTCAGGATTGAAGACGATATGGGGGAGATTGAGAGGCCATGAGAGAATTGTTCGT       218
       R  Y  V  L  S  Q  N  L  R  I  E  D  D  M  D  G  G  D  W  S  F  C  D  G  R  L  R  G  H  E  K  F
 701 TGGCTCTTGCCAGCAAGGTGTAGCAGCACTTTACTAAAGACTTTACTGTATTTGGAGCCCGGTACTTATAACTGGAAAGGATTGTTCGT       252
       G  S  C  Q  G  V  A  A  T  F  T  K  D  F  H  Y  I  V  F  G  A  P  G  T  Y  N  W  K  G  I  V  R
 801 GTAGAGCAAAAGAATAACACTTTTAGGTTTTTCTTTGGACTTGTTTCTAAAGATGAGATCACTTTTGTATCTGGTGCTCCAGAGCCAATCA       285
       V  E  Q  K  N  N  T  F  F  D  M  N  I  F  E  D  G  P  Y  E  V  G  G  E  T  E  H  D  E  S  L  V  P  V
 901 TTCCTGCTAACAGTACTTAGGTTTTCTTTGGACTTGTTTCTAAAGATGAGATCACTTTTGTATCTGGTGCTCCAGAGCCAATCA       318
       P  A  N  S  Y  L  G  F  S  L  D  S  G  K  G  I  V  S  K  D  E  I  T  F  V  S  G  A  P  R  A  N  H
1001 CAGTGGAGCCGTGGTTTGCTGAAGAGACATGAAGTCTGCACATCTCCCTGAGCACATATTCGATGGAGAAGGTCTGGCCTTCTTCATTGGCTAT       352
       S  G  A  V  V  L  L  K  R  D  M  K  S  A  H  L  L  P  E  H  I  F  D  G  E  G  L  A  S  S  F  G  Y
1101 GATGTGGCGGTGATGGACCTCAACAAGGATGGTGGCAAGATATAGTTATTGGAGCCCCACAGTATTTTGATAGAGATGGAGAAGTTGGAGGTGCAGTGT       385
       D  V  A  V  M  D  L  N  K  D  G  W  Q  D  I  V  I  G  A  P  Q  Y  F  D  R  D  G  E  V  G  G  A  V  Y
1201 ATGTCTACATGAACCAGCAAGGCAGATGGAATAATGTGAAGCCAATTCGTCTTAATGAACAAAGATTCTATGTTTGGCATTGCAGTAAAAATATTGG
       V  Y  M  N  Q  Q  G  R  W  N  N  V  K  P  I  R  L  N  G  T  K  D  S  M  F  G  I  A  V  K  N  I  G
```

```
4301 ATTAGAGCATGGGAGGGTCATCACTATGACCTAAATTATTACTGCAAAAGAGAAATCTTTATAAATGTACCAGAGAGAGTTGTTTAATAACTTATCTA
4401 TAAACTATAACCTCTCCTTCATGACAGCCTCCACCCCACAACCCAAAAGGTTAAGAAATAGAATTAACTGTAAAGATGTTTATTTCAGGCATTGGAT
4501 ATTTTTACTTTAGAAGCCTGCATAATACTGTTTCTGGATTTACATACTGTAACATTCAGGAATTCTTGGAGAAGATGGGTTTATTCACTGAACTCTAGTGCG
4601 GTTACTCACTGCTGCAAATACTGTATATTCAGGACTTGAAATGGTGAATGCCTATGGAACTAGTGGATCCAAACTGATCCAGTATAAGACTACTG
4701 AATCTGCTACCAAAACAGTTAATCAGTGAGTCGAGTGTTCTATTTTGTTCCTCCCTATCTGTATTCCAAAAATTACTTTGGGCTAATTT
4801 AACAAGAACTTAAATTGTGTTTAATTGTAAAAATGGCAGGGGTGGAATTATTACTCAACAGAGACTGAATAGATATGAAAGCTGATTT
4901 TTTTAATTACCATGCTTCACAATGTTAAGTTATATGGGGAGCAACAGCAAACAGGTGCTAATTGTTTGGATATAGTATAAGCAGTGTCTGTTTG
5001 AAAGAATAGAACACAGTTGAATTCTTAGTCACAAAATATATTTGTTTACAACAGGTTATAACAGTGTTAAAGTCTCAGTTCTTCTGCTTG
5101 TTGGTTGTACTTGGAATTCTTGGAATTCTCACAAAATATATTTGTCAAAACAGGTTATAACAGTGTTAAAGTCTCAGTTTCTTCTGCTTG
5201 GGGAACTTGTGTCCCTAATGTGTTAGATTGCTAGATGACAGTTTTTAGACCTGTGTTACTAACAAAAAAGATGAATGTCGG
5301 AAAAGGGTGTTGGGAGGGTGGTCAACAAGAAACAAAGATGTTATGGTGTTAGACTTGTTAAAAATGTCATCTCAAGTCAAGTCAAGTCACTGGTCTG
5401 TTTGCATTTGATACATTTTGTACTAACTAGCATTGTAAAATTATTTCATGATTAGAAATTCATGATTAGAAATTCATGATATTTGTATAAAAGTGTGAATAATTTT
5501 TATAAAAGTGTTCATTGTTTCGTAACACAGCATTGTATATGTGAAGCAAACTCTAAAATTATAAATGACAACCTGAATTATCTATTTCATCAAAAAAAA
5601 AAAAAAAAAAAAACTTTATGGGCACAACTGG
```

FIG.6D

```
  1 GCGCTGCCCGCCTCGTCCCCACCCCCCAACCCCCCGCGCCCGCCCTCGGACAGTCCCTGC
    TCGCCCGCGCGCTGCAGCCCCATCTCCTAGCGGCAGCCCAGGCGCGGAGGGAGCGAGTCC

121 GCCCCGAGG TAGGTCCAGGACGGGCGCACAGCAGCAGCCGAGGCTGGCCGGGAGAGGG AG
    GAAGAGGATGGCAGGGCCACGCCCCAGCCCATGGGCCAGGCTGCTCCTGGCAGCCTTGAT
             M  A  G  P  R  P  S  P  W  A  R  L  L  L  A  A  L  I   18

241 CAGCGTCAGCCTCTCTGGGACCTTGGCAAACCGCTGCAAGAAGGCCCCAGTGAAGAGCTG
     S  V  S  L  S  G  T  L  A  N  R  C  K  K  A  P  V  K  S  C

CACGGAGTGTGTCCGTGTGGATAAGGACTGCGCCTACTGCACAGACGAGATGTTCAGGGA
     T  E  C  V  R  V  D  K  D  C  A  Y  C  T  D  E  M  F  R  D  58

361 CCGGCGCTGCAACACCCAGGCGGAGCTGCTGGCCGCGGGCTGCCAGCGGGAGAGCATCGT
     R  R  C  N  T  Q  A  E  L  L  A  A  G  C  Q  R  E  S  I  V

GGTCATGGAGAGCAGCTTCCAAATCACAGAGGAGACCCAGATTGACACCACCCTG.....
     V  M  E  S  S  F  Q  I  T  E  E  T  Q  I  D  T  T  L ...... 96

............................................................
    ............................................................

2288 .......CACAAGAAGAAGGACTGCCCTCCGGGCTCCTTCTGGTGGCTCATCCCCCTGCT
     ...... H  K  K  K  D  C  P  P  G  S  F  W  W  L  I  P  L  L

CCTCCTCCTCCTGCCGCTCCTGGCCCTGCTACTGCTGCTATGCTGGAAGTACTGT.....
     L  L  L  L  P  L  L  A  L  L  L  L  C  W  K  Y  C ...... 736

............................................................
    ............................................................

4085 ....GCGCGCAACGGGGCCGGCTGGGGGCCTGAGCGGGAGGCCATCATCAACCTGGCCAC
     ... A  R  N  G  A  G  W  G  P  E  R  E  A  I  I  N  L  A  T

CCAGCCCAAGAGGCCCATGTCCATCCCCATCATCCCTGACATCCCTATCGTGGACGCCCA
     Q  P  K  R  P  M  S  I  P  I  I  P  D  I  P  I  V  D  A  Q  1338

4201 GAGCGGGGAGGACTACGACAGCTTCCTTATGTACAGCGATGACGTTCTACGCTCTCCATC
     S  G  E  D  Y  D  S  F  L  M  Y  S  D  D  V  L  R  S  P  S

GGGCAGCCAGAGGCCCAGCGTCTCCGATGACACT GGCTGCGGCTGGAAGTTCGAGCCCCT
     G  S  Q  R  P  S  V  S  D  D  T   G  C  G  W  K  F  E  P  L  1378
```

FIG. 8A

```
4321 GCTGGGGGAGGAGCTGGACCTGCGGCGCGTCACGTGGCGGCTGCCCCCGGAGCTCATCCC
      L  G  E  E  L  D  L  R  R  V  T  W  R  L  P  P  E  L  I  P

GCGCCTGTCGGCCAGCAGCGGGCGCTCCTCCGACGCCGAGGCCCCCACGGCCCCCCGGAC
      R  L  S  A  S  S  G  R  S  S  D  A  E  A  P  T  A  P  R  T   1418

4441 GACGGCGGCGCGGGCGGGAAGGGCGGCAGCCGTGCCCCGCAGTGCGACACCCGGGCCCC
      T  A  A  R  A  G  R  A  A  A  V  P  R  S  A  T  P  G  P  P

CGGAGAGCACCTGGTGAATGGCCGGATGGACTTTGCCTTCCCGGGCAGCACCAACTCCCT
      G  E  H  L  V  N  G  R  M  D  F  A  F  P  G  S  T  N  S  L   1458

4561 GCACAGGATGACCACGACCAGTGCTGCTGCCTATGGCACCCACCTGAGCCCACACGTGCC
      H  R  M  T  T  S  A  A  A  Y  G  T  H  L  S  P  H  V  P

CCACCGCGTGCTAAGCACATCCTCCACCCTCACACGGGACTACAACTCACTGACCCGCTC
      H  R  V  L  S  T  S  S  T  L  T  R  D  Y  N  S  L  T  R  S   1498

4681 AGAACACTCACACTCGACCACACTGCCCAGGGACTACTCCACCCTCACCTCCGTCTCCTC
      E  H  S  H  S  T  T  L  P  R  D  Y  S  T  L  T  S  V  S  S

CCACGACTCTCGCCTGACTGCTGGTGTGCCCGACACGCCCACCCGCCTGGTGTTCTCTGC
      H  D  S  R  L  T  A  G  V  P  D  T  P  T  R  L  V  F  S  A   1538

4801 CCTGGGGCCCACATCTCTCAGAGTGAGCTGGCAGGAGCCGCGGTGCGAGCGGCCGCTGCA
      L  G  P  T  S  L  R  V  S  W  Q  E  P  R  C  E  R  P  L  Q

GGGCTACAGTGTGGAGTACCAGCTGCTGAACGGCGGTGAGCTGCATCGGCTCAAC.....
      G  Y  S  V  E  Y  Q  L  L  N  G  G  E  L  H  R  L  N  .....  1576
     .............................................................
     .............................................................

5525 ....ACCCTGGGGGCCCAGCACCTGGAGGCAGGCGGCTCCCTCACCCGGCATGTGACCCA
      ..  T  L  G  A  Q  H  L  E  A  G  G  S  L  T  R  H  V  T  Q

GGAGTTTGTGAGCCGGACACTGACCACCAGCGGAACCCTTAGCACCCACATGGACCAACA
      E  F  V  S  R  T  L  T  T  S  G  T  L  S  T  H  M  D  Q  Q   1818

5641 GTTCTTCCAAACTTGACCGCACCCTGCCCCACCCCCGCCATGTCCCACTAGGCGTCCTCC
      F  F  Q  T  *

CGACTCCTCTCCCGGAGCCTCCTCAGCTACTCCATCCTTGCACCCCTGGGGGCCCAGCCC
                                                                   1822

5761 ACCCGCATGCACAGAGCAGGGGCTAGGTGTCTCCTGGGAGGCATGAAGGGGGCAAGGTCC
     GTCCTCTGTGGGCCCAAACCTATTTGTAACCAAAGAGCTGGGAGCAGCACAAGGACCCAG

5881 CCTTTGTTCTGCACTTAATAAATGGTTTTGCTACTGCTAAAAAAAAAAAAAAAAAAAAAA
     AAAAAAAAAAAAAAAAAAAAAAAAAAAAAAAAAAAAAAAAAAAAAAAAAAAAAAAAAA
```

FIG. 8B

```
  1 GCGCTGCCCGCCTCGTCCCCACCCCCCAACCCCCCGCGCCCGCCCTCGGACAGTCCCTGC
    TCGCCCGCGCGCTGCAGCCCCATCTCCTAGCGGCAGCCCAGGCGCGGAGGGAGCGAGTCC
121 GCCCCGAGG TAGGTCCAGGACGGGCGCACAGCAGCAGCCGAGGCTGGCCGGGAGAGGG AG
    GAAGAGGATGGCAGGGCCACGCCCCAGCCCATGGGCCAGGCTGCTCCTGGCAGCCTTGAT
              M A G P R P S P W A R L L L A A L I         18
241 CAGCGTCAGCCTCTCTGGGACCTTGGCAAACCGCTGCAAGAAGGCCCCAGTGAAGAGCTG
    S V S L S G T L A N R C K K A P V K S C
    CACGGAGTGTGTCCGTGTGGATAAGGACTGCGCCTACTGCACAGACGAGATGTTCAGGGA
    T E C V R V D K D C A Y C T D E M F R D         58
361 CCGGCGCTGCAACACCCAGGCGGAGCTGCTGGCCGCGGGCTGCCAGCGGGAGAGCATCGT
    R R C N T Q A E L L A A G C Q R E S I V
    GGTCATGGAGAGCAGCTTCCAAATCACAGAGGAGACCCAGATTGACACCACCCTGCGGCG
    V M E S S F Q I T E E T Q I D T T L R R         98
481 CAGCCAGATGTCCCCCCAAGGCCTGCGGGTCCGTCTGCGGCCCGGTGAGGAGCGGCATTT
    S Q M S P Q G L R V R L R P G E E R H F
    TGAGCTGGAGGTGTTTGAGCCACTGGAGAGCCCCGTGGACCTGTACATCCTCATGGACTT
    E L E V F E P L E S P V D L Y I L M D F        138
601 CTCCAACTCCATGTCCGATGATCTGGACAACCTCAAGAAGATGGGGCAGAACCTGGCTCG
    S N S M S D D L D N L K K M G Q N L A R
    GGTCCTGAGCCAGCTCACCAGCGACTACACTATTGGATTTGGCAAGTTTGTGGACAAAGT
    V L S Q L T S D Y T I G F G K F V D K V        178
721 CAGCGTCCCGCAGACGGACATGAGGCCTGAGAAGCTGAAGGAGCCCTGGCCCAACAGTGA
    S V P Q T D M R P E K L K E P W P N S D
    CCCCCCCTTCTCCTTCAAGAACGTCATCAGCCTGACAGAAGATGTGGATGAGTTCCGGAA
    P P F S F K N V I S L T E D V D E F R N        218
841 TAAACTGCAGGGAGAGCGGATCTCAGGCAACCTGGATGCTCCTGAGGGCGGCTTCGATGC
    K L Q G E R I S G N L D A P E G G F D A
    CATCCTGCAGACAGCTGTGTGCACGAGGGACATTGGCTGGCGCCCGGACAGCACCCACCT
    I L Q T A V C T R D I G W R P D S T H L        258
961 GCTGGTCTTCTCCACCGAGTCAGCCTTCCACTATGAGGCTGATGGCGCCAACGTGCTGGC
    L V F S T E S A F H Y E A D G A N V L A
    TGGCATCATGAGCCGCAACGATGAACGGTGCCACCTGGACACCACGGGCACCTACACCCA
    G I M S R N D E R C H L D T T G T Y T Q        298
1081 GTACAGGACACAGGACTACCCGTCGGTGCCCACCCTGGTGCGCCTGCTCGCCAAGCACAA
    Y R T Q D Y P S V P T L V R L L A K H N
    CATCATCCCCATCTTTGCTGTCACCAACTACTCCTATAGCTACTACGAGAAGCTTCACAC
    I I P I F A V T N Y S Y S Y Y E K L H T        338
1201 CTATTTCCCTGTCTCCTCACTGGGGGTGCTGCAGGAGGACTCGTCCAACATCGTGGAGCT
    Y F P V S S L G V L Q E D S S N I V E L
    GCTGGAGGAGGCCTTCAATCGGATCCGCTCCAACCTGGACATCCGGGCCCTAGACAGCCC
    L E E A F N R I R S N L D I R A L D S P        378
```

FIG.9A

```
1321 CCGAGGCCTTCGGACAGAGGTCACCTCCAAGATGTTCCAGAAGACGAGGACTGGGTCCTT
      R  G  L  R  T  E  V  T  S  K  M  F  Q  K  T  R  T  G  S  F
     TCACATCCGGCGGGGGGAAGTGGGTATATACCAGGTGCAGCTGCGGGCCCTTGAGCACGT
      H  I  R  R  G  E  V  G  I  Y  Q  V  Q  L  R  A  L  E  H  V  418
1441 GGATGGGACGCACGTGTGCCAGCTGCCGGAGGACCAGAAGGGCAACATCCATCTGAAACC
      D  G  T  H  V  C  Q  L  P  E  D  Q  K  G  N  I  H  L  K  P
     TTCCTTCTCCGACGGCCTCAAGATGGACGCGGGCATCATCTGTGATGTGTGCACCTGCGA
      S  F  S  D  G  L  K  M  D  A  G  I  I  C  D  V  C  T  C  E  458
1561 GCTGCAAAAAGAGGTGCGGTCAGCTCGCTGCAGCTTCAACGGAGACTTCGTGTGCGGACA
      L  Q  K  E  V  R  S  A  R  C  S  F  N  G  D  F  V  C  G  Q
     GTGTGTGTGCAGCGAGGGCTGGAGTGGCCAGACCTGCAACTGCTCCACCGGCTCTCTGAG
      C  V  C  S  E  G  W  S  G  Q  T  C  N  C  S  T  G  S  L  S  498
1681 TGACATTCAGCCCTGCCTGCGGGAGGGCGAGGACAAGCCGTGCTCCGGCCGTGGGGAGTG
      D  I  Q  P  C  L  R  E  G  E  D  K  P  C  S  G  R  G  E  C
     CCAGTGCGGGCACTGTGTGTGCTACGGCGAAGGCCGCTACGAGGGTCAGTTCTGCGAGTA
      Q  C  G  H  C  V  C  Y  G  E  G  R  Y  E  G  Q  F  C  E  Y  538
1801 TGACAACTTCCAGTGTCCCCGCACTTCCGGGTTCCTGTGCAATGACCGAGGACGCTGCTC
      D  N  F  Q  C  P  R  T  S  G  F  L  C  N  D  R  G  R  C  S
     CATGGGCCAGTGTGTGTGTGAGCCTGGTTGGACAGGCCCAAGCTGTGACTGTCCCCTCAG
      M  G  Q  C  V  C  E  P  G  W  T  G  P  S  C  D  C  P  L  S  578
1921 CAATGCCACCTGCATCGACAGCAATGGGGGCATCTGTAATGGACGTGGCCACTGTGAGTG
      N  A  T  C  I  D  S  N  G  G  I  C  N  G  R  G  H  C  E  C
     TGGCCGCTGCCACTGCCACCAGCAGTCGCTCTACACGGACACCATCTGCGAGATCAACTA
      G  R  C  H  C  H  Q  Q  S  L  Y  T  D  T  I  C  E  I  N  Y  618
2041 CTCGGCGATCCACCCGGGCCTCTGCGAGGACCTACGCTCCTGCGTGCAGTGCCAGGCGTG
      S  A  I  H  P  G  L  C  E  D  L  R  S  C  V  Q  C  Q  A  W
     GGGCACCGGCGAGAAGAAGGGGCGCACGTGTGAGGAATGCAACTTCAAGGTCAAGATGGT
      G  T  G  E  K  K  G  R  T  C  E  E  C  N  F  K  V  K  M  V  658
2161 GGACGAGCTTAAGAGAGCCGAGGAGGTGGTGGTGCGCTGCTCCTTCCGGGACGAGGATGA
      D  E  L  K  R  A  E  E  V  V  V  R  C  S  F  R  D  E  D  D
     CGACTGCACCTACAGCTACACCATGGAAGGTGACGGCGCCCCTGGGCCCAACAGCACTGT
      D  C  T  Y  S  Y  T  M  E  G  D  G  A  P  G  P  N  S  T  V  698
2281 CCTGGTGCACAAGAAGAAGGACTGCCCCTCCGGGCTCCTTCTGGTGGCTCATCCCCCTGCT
      L  V  H  K  K  K  D  C  P  P  G  S  F  W  W  L  I  P  L  L
     CCTCCTCCTCCTGCCGCTCCTGGCCCTGCTACTGCTGCTATGCTGGAAGTACTGTGCCTG
      L  L  L  L  P  L  L  A  L  L  L  L  C  W  K  Y  C  A  C  738
2401 CTGCAAGGCCTGCCTGGCACTTCTCCCGTGCTGCAACCGAGGTCACATGGTGGGCTTTAA
      C  K  A  C  L  A  L  L  P  C  C  N  R  G  H  M  V  G  F  K
     GGAAGACCACTACATGCTGCGGGAGAACCTGATGGCCTCTGACCACTTGGACACGCCCAT
      E  D  H  Y  M  L  R  E  N  L  M  A  S  D  H  L  D  T  P  M  778

2521 GCTGCGCAGCGGGAACCTCAAGGGCCGTGACGTGGTCCGCTGGAAGGTCACCAACAACAT
      L  R  S  G  N  L  K  G  R  D  V  V  R  W  K  V  T  N  N  M
     GCAGCGGCCTGGCTTTGCCACTCATGCCGCCAGCATCAACCCCACAGAGCTGGTGCCCTA
      Q  R  P  G  F  A  T  H  A  A  S  I  N  P  T  E  L  V  P  Y  818
```

FIG.9B

```
2641 CGGGCTGTCCTTGCGCCTGGCCCGCCTTTGCACCGAGAACCTGCTGAAGCCTGACACTCG
      G  L  S  L  R  L  A  R  L  C  T  E  N  L  L  K  P  D  T  R
     GGAGTGCGCCCAGCTGCGCCAGGAGGTGGAGGAGAACCTGAACGAGGTCTACAGGCAGAT
      E  C  A  Q  L  R  Q  E  V  E  E  N  L  N  E  V  Y  R  Q  I   858
2761 CTCCGGTGTACACAAGCTCCAGCAGACCAAGTTCCGGCAGCAGCCCAATGCCGGGAAAAA
      S  G  V  H  K  L  Q  Q  T  K  F  R  Q  Q  P  N  A  G  K  K
     GCAAGACCACACCATTGTGGACACAGTGCTGATGGCGCCCCGCTCGGCCAAGCCGGCCCT
      Q  D  H  T  I  V  D  T  V  L  M  A  P  R  S  A  K  P  A  L   898
2881 GCTGAAGCTTACAGAGAAGCAGGTGGAACAGAGGGCCTTCCACGACCTCAAGGTGGCCCC
      L  K  L  T  E  K  Q  V  E  Q  R  A  F  H  D  L  K  V  A  P
     CGGCTACTACACCCTCACTGCAGACCAGGACGCCCGGGGCATGGTGGAGTTCCAGGAGGG
      G  Y  Y  T  L  T  A  D  Q  D  A  R  G  M  V  E  F  Q  E  G   938
3001 CGTGGAGCTGGTGGACGTACGGGTGCCCCTCTTTATCCGGCCTGAGGATGACGACGAGAA
      V  E  L  V  D  V  R  V  P  L  F  I  R  P  E  D  D  D  E  K
     GCAGCTGCTGGTGGAGGCCATCGACGTGCCCGCAGGCACTGCCACCCTCGGCCGCCGCCT
      Q  L  L  V  E  A  I  D  V  P  A  G  T  A  T  L  G  R  R  L   978
3121 GGTAAACATCACCATCATCAAGGAGCAAGCCAGAGACGTGGTGTCCTTTGAGCAGCCTGA
      V  N  I  T  I  I  K  E  Q  A  R  D  V  V  S  F  E  Q  P  E
     GTTCTCGGTCAGCCGCGGGGACCAGGTGGCCCGCATCCCTGTCATCCGGCGTGTCCTGGA
      F  S  V  S  R  G  D  Q  V  A  R  I  P  V  I  R  R  V  L  D   1018
3241 CGGCGGGAAGTCCCAGGTCTCCTACCGCACACAGGATGGCACCGCGCAGGGCAACCGGGA
      G  G  K  S  Q  V  S  Y  R  T  Q  D  G  T  A  Q  G  N  R  D
     CTACATCCCCGTGGAGGGTGAGCTGCTGTTCCAGCCTGGGGAGGCCTGGAAAGAGCTGCA
      Y  I  P  V  E  G  E  L  L  F  Q  P  G  E  A  W  K  E  L  Q   1058
3361 GGTGAAGCTCCTGGAGCTGCAAGAAGTTGACTCCCTCCTGCGGGGCCGCCAGGTCCGCCG
      V  K  L  L  E  L  Q  E  V  D  S  L  L  R  G  R  Q  V  R  R
     TTTCCACGTCCAGCTCAGCAACCCTAAGTTTGGGGCCCACCTGGGCCAGCCCCACTCCAC
      F  H  V  Q  L  S  N  P  K  F  G  A  H  L  G  Q  P  H  S  T   1098
3481 CACCATCATCATCAGGGACCCAGATGAACTGGACCGGAGCTTCACGAGTCAGATGTTGTC
      T  I  I  I  R  D  P  D  E  L  D  R  S  F  T  S  Q  M  L  S
     ATCACAGCCACCCCCTCACGGCGACCTGGGCGCCCCGCAGAACCCCAATGCTAAGGCCGC
      S  Q  P  P  P  H  G  D  L  G  A  P  Q  N  P  N  A  K  A  A   1138
3601 TGGGTCCAGGAAGATCCATTTCAACTGGCTGCCCCCTTCTGGCAAGCCAATGGGGTACAG
      G  S  R  K  I  H  F  N  W  L  P  P  S  G  K  P  M  G  Y  R
     GGTAAAGTACTGGATTCAGGGCGACTCCGAATCCGAAGCCCACCTGCTCGACAGCAAGGT
      V  K  Y  W  I  Q  G  D  S  E  S  E  A  H  L  L  D  S  K  V   1178
```

FIG.9C

```
3721 GCCCTCAGTGGAGCTCACCAACCTGTACCCGTATTGCGACTATGAGATGAAGGTGTGCGC
      P  S  V  E  L  T  N  L  Y  P  Y  C  D  Y  E  M  K  V  C  A
     CTACGGGGCTCAGGGCGAGGGACCCTACAGCTCCCTGGTGTCCTGCCGCACCCACCAGGA
      Y  G  A  Q  G  E  G  P  Y  S  S  L  V  S  C  R  T  H  Q  E   1218
3841 AGTGCCCAGCGAGCCAGGGCGTCTGGCCTTCAATGTCGTCTCCTCCACGGTGACCCAGCT
      V  P  S  E  P  G  R  L  A  F  N  V  V  S  S  T  V  T  Q  L
     GAGCTGGGCTGAGCCGGCTGAGACCAACGGTGAGATCACAGCCTACGAGGTCTGCTATGG
      S  W  A  E  P  A  E  T  N  G  E  I  T  A  Y  E  V  C  Y  G   1258
3961 CCTGGTCAACGATGACAACCGACCTATTGGGCCCATGAAGAAAGTGCTGGTTGACAACCC
      L  V  N  D  D  N  R  P  I  G  P  M  K  K  V  L  V  D  N  P
     TAAGAACCGGATGCTGCTTATTGAGAACCTTCGGGAGTCCCAGCCCTACCGCTACACGGT
      K  N  R  M  L  L  I  E  N  L  R  E  S  Q  P  Y  R  Y  T  V   1298
4081 GAAGGCGCGCAACGGGGCCGGCTGGGGGCCTGAGCGGGAGGCCATCATCAACCTGGCCAC
      K  A  R  N  G  A  G  W  G  P  E  R  E  A  I  I  N  L  A  T
     CCAGCCCAAGAGGCCCATGTCCATCCCCATCATCCCTGACATCCCTATCGTGGACGCCCA
      Q  P  K  R  P  M  S  I  P  I  I  P  D  I  P  I  V  D  A  Q   1338
4201 GAGCGGGGAGGACTACGACAGCTTCCTTATGTACAGCGATGACGTTCTACGCTCTCCATC
      S  G  E  D  Y  D  S  F  L  M  Y  S  D  D  V  L  R  S  P  S
     GGGCAGCCAGAGGCCCAGCGTCTCCGATGACACTGGCTGCGGCTGGAAGTTCGAGCCCCT
      G  S  Q  R  P  S  V  S  D  D  T  G  C  G  W  K  F  E  P  L   1378
4321 GCTGGGGGAGGAGCTGGACCTGCGGCGCGTCACGTGGCGGCTGCCCCCGGAGCTCATCCC
      L  G  E  E  L  D  L  R  R  V  T  W  R  L  P  P  E  L  I  P
     GCGCCTGTCGGCCAGCAGCGGGCGCTCCTCCGACGCCGAGGCCCCCACGGCCCCCCGGAC
      R  L  S  A  S  S  G  R  S  S  D  A  E  A  P  T  A  P  R  T   1418
4441 GACGGCGGCGCGGGCGGGAAGGGCGGCAGCCGTGCCCCGCAGTGCGACACCCGGGCCCCC
      T  A  A  R  A  G  R  A  A  A  V  P  R  S  A  T  P  G  P  P
     CGGAGAGCACCTGGTGAATGGCCGGATGGACTTTGCCTTCCCGGGCAGCACCAACTCCCT
      G  E  H  L  V  N  G  R  M  D  F  A  F  P  G  S  T  N  S  L   1458
4561 GCACAGGATGACCACGACCAGTGCTGCTGCCTATGGCACCCACCTGAGCCCACACGTGCC
      H  R  M  T  T  T  S  A  A  A  Y  G  T  H  L  S  P  H  V  P
     CCACCGCGTGCTAAGCACATCCTCCACCCTCACACGGGACTACAACTCACTGACCCGCTC
      H  R  V  L  S  T  S  S  T  L  T  R  D  Y  N  S  L  T  R  S   1498
4681 AGAACACTCACACTCGACCACACTGCCCAGGGACTACTCCACCCTCACCTCCGTCTCCTC
      E  H  S  H  S  T  T  L  P  R  D  Y  S  T  L  T  S  V  S  S
     CCACGACTCTCGCCTGACTGCTGGTGTGCCCGACACGCCCACCCGCCTGGTGTTCTCTGC
      H  D  S  R  L  T  A  G  V  P  D  T  P  T  R  L  V  F  S  A   1538
4801 CCTGGGGCCCACATCTCTCAGAGTGAGCTGGCAGGAGCCGCGGTGCGAGCGGCCGCTGCA
      L  G  P  T  S  L  R  V  S  W  Q  E  P  R  C  E  R  P  L  Q
     GGGCTACAGTGTGGAGTACCAGCTGCTGAACGGCGGTGAGCTGCATCGGCTCAACATCCC
      G  Y  S  V  E  Y  Q  L  L  N  G  G  E  L  H  R  L  N  I  P   1578
4921 CAACCCTGCCCAGACCTCGGTGGTGGTGGAAGACCTCCTGCCCAACCACTCCTACGTGTT
      N  P  A  Q  T  S  V  V  V  E  D  L  L  P  N  H  S  Y  V  F
     CCGCGTGCGGGCCCAGAGCCAGGAAGGCTGGGGCCGAGAGCGTGAGGGTGTCATCACCAT
      R  V  R  A  Q  S  Q  E  G  W  G  R  E  R  E  G  V  I  T  I   1618
```

FIG.9D

```
5041 TGAATCCCAGGTGCACCCGCAGAGCCCACTGTGTCCCTGCCAGGCTCCGCCTTCACTTT
      E  S  Q  V  H  P  Q  S  P  L  C  P  L  P  G  S  A  F  T  L
     GAGCACTCCCAGTGCCCCAGGCCCGCTGGTGTTCACTGCCCTGAGCCCAGACTCGCTGCA
      S  T  P  S  A  P  G  P  L  V  F  T  A  L  S  P  D  S  L  Q  1658
5161 GCTGAGCTGGGAGCGGCCACGGAGGCCCAATGGGGATATCGTCGGCTACCTGGTGACCTG
      L  S  W  E  R  P  R  R  P  N  G  D  I  V  G  Y  L  V  T  C
     TGAGATGGCCCAAGGAGGAGGGCCAGCCACCGCATTCCGGGTGGATGGAGACAGCCCCGA
      E  M  A  Q  G  G  G  P  A  T  A  F  R  V  D  G  D  S  P  E  1698
5281 GAGCCGGCTGACCGTGCCGGGCCTCAGCGAGAACGTGCCCTACAAGTTCAAGGTGCAGGC
      S  R  L  T  V  P  G  L  S  E  N  V  P  Y  K  F  K  V  Q  A
     CAGGACCACTGAGGGCTTCGGGCCAGAGCGCGAGGGCATCATCACCATAGAGTCCCAGGA
      R  T  T  E  G  F  G  P  E  R  E  G  I  I  T  I  E  S  Q  D  1738
5401 TGGAGGACCCTTCCCGCAGCTGGGCAGCCGTGCCGGGCTCTTCCAGCACCCGCTGCAAAG
      G  G  P  F  P  Q  L  G  S  R  A  G  L  F  Q  H  P  L  Q  S
     CGAGTACAGCAGCATCACCACCACCCACACCAGCGCCACCGAGCCCTTCCTAGTGGATGG
      E  Y  S  S  I  T  T  T  H  T  S  A  T  E  P  F  L  V  D  G  1778
5521 GCTGACCCTGGGGGCCCAGCACCTGGAGGCAGGCGGCTCCCTCACCCGGCATGTGACCCA
      L  T  L  G  A  Q  H  L  E  A  G  G  S  L  T  R  H  V  T  Q
     GGAGTTTGTGAGCCGGACACTGACCACCAGCGGAACCCTTAGCACCCACATGGACCAACA
      E  F  V  S  R  T  L  T  T  S  G  T  L  S  T  H  M  D  Q  Q  1818
5641 GTTCTTCCAAACTTGACCGCACCCTGCCCCACCCCCGCCATGTCCCACTAGGCGTCCTCC
      F  F  Q  T  *
     CGACTCCTCTCCCGGAGCCTCCTCAGCTACTCCATCCTTGCACCCCTGGGGGCCCAGCCC
                                                                 1822
5761 ACCCGCATGCACAGAGCAGGGGCTAGGTGTCTCCTGGGAGGCATGAAGGGGGCAAGGTCC
     GTCCTCTGTGGGCCCAAACCTATTTGTAACCAAAGAGCTGGGAGCAGCACAAGGACCCAG
5881 CCTTTGTTCTGCACTTAATAAATGGTTTTGCTACTGCTAAAAAAAAAAAAAAAAAAAAAA
     AAAAAAAAAAAAAAAAAAAAAAAAAAAAAAAAAAAAAAAAAAAAAAAAAAAA
```

FIG.9E

FIG.11A
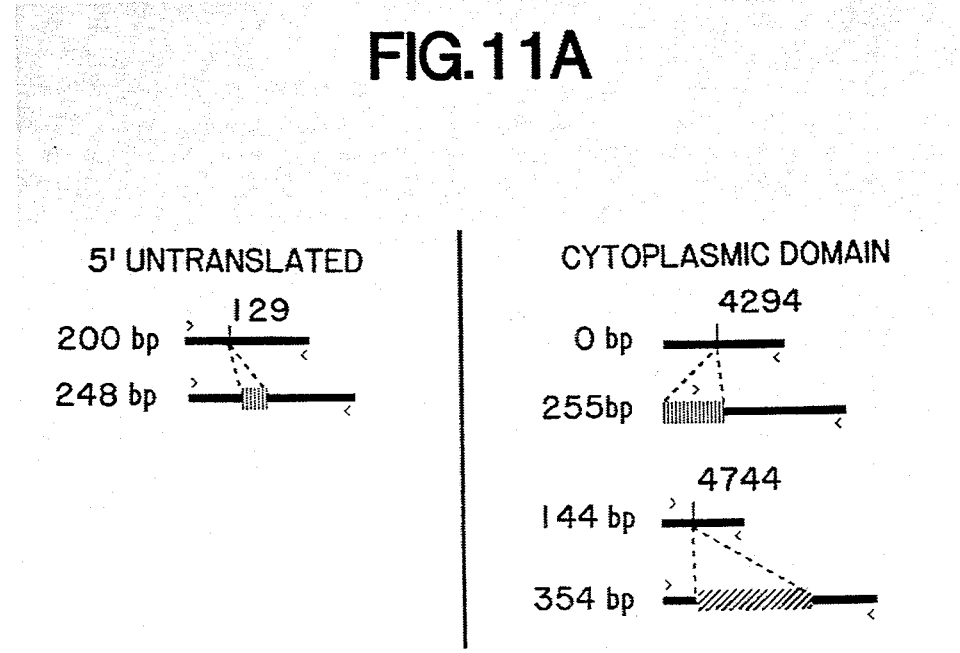
FIG.11B

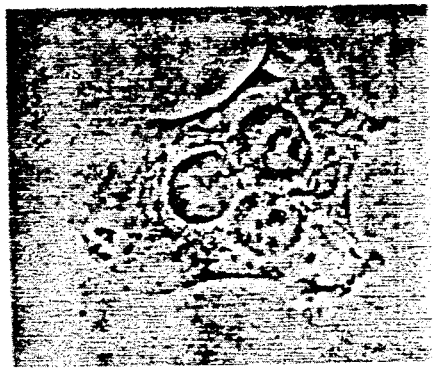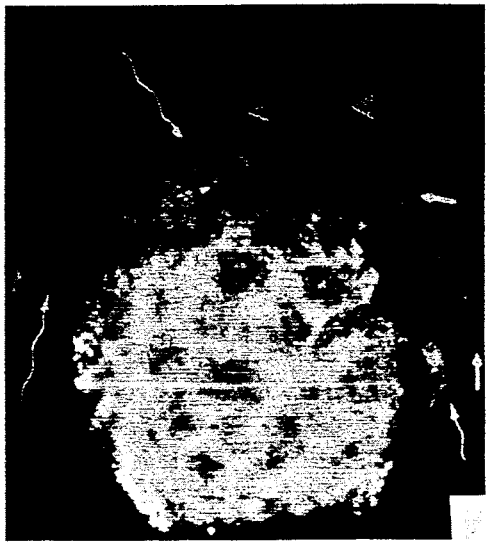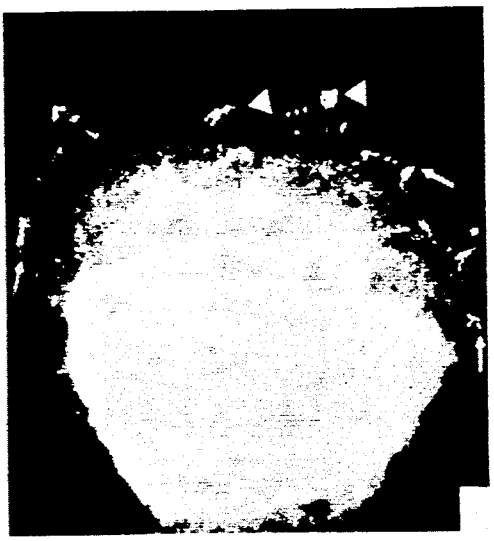

METHOD OF DIAGNOSING THE PRESENCE OF ABNORMAL EPITHELIAL TISSUE USING MONOCLONAL ANTIBODIES TO THE $A_6B_4$ CELL SURFACE PROTEIN

This invention was made with government support under Grant No. 1R01 CA47858 from the National Institutes of Health. The government has certain rights in the invention.

CROSS-REFERENCE TO RELATED APPLICATIONS

This is a continuation-in-part of U.S. Ser. No. 07/293,384, filed Jan. 4, 1989, now abandoned in favor of continuation application U.S. Ser. No. 08/014,090, filed Feb. 4, 1993, which abandoned application is a continuation-in-part of U.S. Ser. No. 07/016,552, filed Feb. 19, 1987, now abandoned in favor of continuation application U.S. Ser. No. 07/333,848, filed Feb. 4, 1989, now issued U.S. Pat. No. 4,962,048, all of which are hereby incorporated herein by reference.

BACKGROUND OF THE INVENTION

The present invention relates generally to a novel antigen and to novel hybridoma cell lines, and more specifically to monoclonal cell lines producing monoclonal antibodies reactive with the novel antigen, which antigen can be found, inter alia, on human pancreatic cancer cells.

Cancer currently constitutes the second most common cause of death in the United States. Carcinomas of the pancreas are the eighth most prevalent form of cancer and fourth among the most common causes of cancer deaths in this country. The incidence of pancreatic cancer has been increasing steadily in the past twenty years in most industrialized countries, exhibiting the characteristics of a growing epidemiological problem.

The prognosis for pancreatic carcinoma is, at present, very poor, it displays the lowest five-year survival rate among all cancers. Such prognosis results primarily from delayed diagnosis, due in part to the fact that the early symptoms are shared with other more common abdominal ailments. The diagnosis of pancreatic cancer is often dependent on exploratory surgery, inevitably performed after the disease has advanced considerably.

Substantial efforts have been directed to developing tools useful for early diagnosis of pancreatic and other carcinomas. Nonetheless, a definitive diagnosis is often dependent on exploratory surgery which is inevitably performed after the disease has advanced past the point when early treatment may be effected. One promising method for early diagnosis of various forms of cancer is the identification of specific biochemical moieties, termed antigens present on the surface of cancerous cells. Antibodies which will specifically recognize and bind to the antigens present on the surfaces of cancer cells potentially provide powerful tools for the diagnosis and treatment of the particular malignancy. Tumor specific cell surface antigens have previously been identified for certain melanomas, lymphomas malignancies of the colon and reproductive tract.

There thus exists a great and long-felt need for a cell surface marker which is present on the surface of neoplastic cells, including those of the pancreas, and for antibodies which specifically recognize such a cell surface marker. Such markers and corresponding antibodies would be useful not only in the early detection of pancreatic and other cancers, but in their treatment as well. The present invention satisfies these needs and provides related advantages as well.

Secondly, the interaction of cells with the extracellular matrix is important for the formation, maintenance, and repair of tissues as well as other biological processes such as the metastasis of cancer cells. This cellular adhesion is mediated, in part, by a family of cell surface receptors called integrins (Hynes, (1987) *Cell* 48:549–554; Ruoslahti and Pierschbacher, (1987) *Science* 238:491–497; Buck and Horwitz, (1987) *Ann. Rev. Cell Biol.* 3:179–205). These receptors form a link between the extracellular matrix and the cytoskeleton and may transmit signals from the extracellular to the intracellular environment which affect cell behavior.

Cell adhesion is critical to many biological processes, including embryonal development, tissue repair, immune response, and malignant transformation. (Ekblom, P., et al. (1986) *Ann. Rev. Cell. Biol.* 2:27 47; Yamada, K. M. (1983) *Ann. Rev. Biochem.* 52:761–799; Edelman, G. M. (1983) *Science* 219:450–457.) Several laboratories have recently done biochemical characterization of adhesion receptors for extracellular matrix and plasma proteins such as fibronectin and vitronectin as well as leukocyte adhesion receptors. (Tamkun, J. W., et al. (1986) *Cell* 46:271–282; Damsky, C. H., et al. (1981) *J. Cell. Biol.* 89:173–184; Pytela, R., et al. (1985) *Cell* 40:191–198; Fitzgerald, L. A., et al. (1987) *J. Biol. Chem.* 262:3936–3939; Giancotti, F. G. (1985) *Exp. Cell Res.* 156:182–190; Springer, T. A. (1985) *Nature* 314:540–542.)

These adhesion receptor proteins have been shown to be structurally homologous to each other. (Charo, I. F. (1986) *Proc. Nat'l Acad. Sci. USA* 83:8351–8355; Suzuki, S. (1986) *Proc. Nat'l Acad. Sci. USA* 83:8416–8418; Kishimoto, T. K. (1987) *Cell* 48:681–690; Takada, Y. (1987) *Nature* 326:607–609.) These related molecules have now been organized into a protein superfamily, designated "/integrins", after the chicken fibronectin/laminin receptor. (Hynes, R. O. (1987) *Cell* 48:549–554.)

Integrins are heterodimers comprised of $\alpha$- and $\beta$-subunits that are noncovalently associated, transmembrane glycoproteins. At least 11 $\alpha$-chains (Ruoslahti and Giancotti, (1989) Cancer Cells 1:119–126) and 6 $\beta$-chains (Sheppard et al , (1990) *J. Biol. Chem.* 265:11502–11507) have been recognized in humans. Each $\alpha$-subunit tends to associate with only one type of $\beta$-subunit, but there are several exceptions to this rule (Hemler et al., (1989) *J. Biol. Chem.* 264:6529–6535; Sonnenberg et al., (1988) *Nature* 336:487–489; Kennel et al., (1989) *J. Biol. Chem.* 264:15515–15521; Cheresh et al., (1989) *Cell* 57:59–69; Holzmann et al., (1989) *Cell* 56:37–46; Freed et al., (1989) EMBO 8:2955–2965).

There thus has been a great and long-felt need for an understanding of cell surface markers, such as integrins or cell adhesion receptors, which are present on neoplastic cells, not only those of the pancreas, and for antibodies which specifically recognize such markers. To understand the marker at a molecular level would provide for a refinement in the early detection of cancers or other pathologies involving cell adhesion disorders, such as epithelial disorders, as well as in their treatment. The present invention satisfies these needs and provides additional advantages as well.

SUMMARY OF THE INVENTION

The present invention provides a composition comprising a cell surface marker, said marker comprising a protein substantially homologous to an $\alpha_6$, a $\beta_4$ or an $\alpha_6\beta_4$ protein, or an antigenic portion thereof.

In another aspect, the present invention provides a composition comprising an antibody specifically reactive with a cell surface marker, said marker comprising a protein substantially homologous to an $\alpha_6$ protein, a $\beta_4$ or an $\alpha_6\alpha_4$ protein, or an antigenic portion thereof.

A further aspect of the present invention is a method of diagnosing the presence of abnormal epithelial tissue comprising: (a) contacting a tissue sample with an antibody specifically reactive with a cell surface marker, said marker comprising a protein substantially homologous to either an $\alpha_6$ protein, a $\beta_4$ or an $\alpha_6\beta_4$ protein, or an antigenic portion thereof, (b) locating said bound antibody on said tissue; and (c) determining whether said location of said bound antibody indicates the presence of abnormal epithelium.

A still further aspect of the present invention is a composition comprising a DNA sequence unique to a cell surface marker, said marker comprising a protein substantially homologous to an $\alpha_6$ protein, a $\beta_4$ or an $\alpha_6\beta_4$ protein, or an antigenic portion thereof; to vectors comprising the DNA sequences; and hosts transformed by the vector; and $\alpha_6$, $\beta_4$ or $\alpha_6\beta_4$ produced by these hosts.

In accordance with the present invention there are provided monoclonal antibodies which react specifically with antigenic markers on the surface of HPC cells. In accordance with a further aspect of the invention, there are provided hybridoma cell lines which produce monoclonal antibodies specifically reactive with HPC cell surface markers.

Preferred hybridoma cell lines are those termed S3-41, S3-53, identified by ATCC accession numbers HB 9318 and HB 9319, respectively, and AA3. The monoclonal antibodies produced and the antigens recognized by these cell lines are also a part of the present invention.

It will be appreciated from the foregoing that the present invention provides novel markers for antibodies against HPC and other tumor cells. In one aspect of the invention, the monoclonal antibodies are used for in vitro immunoassays to detect HPC. In another aspect of the invention, the monoclonal antibodies, conjugated with certain detectable labels, are useful as in vivo imaging agents for detecting HPC. Moreover, when conjugated with certain toxins, such monoclonal antibodies are useful for therapeutic treatment of HPC.

Another aspect of the invention concerns the cell surface markers reactive with the antibodies of the invention. These markers are useful in characterization of the cells bearing them and in design of agonists and antagonists of their functions.

The antigens reactive with HB 9318 is (are) a new member of the integrin superfamily. As with other integrins, this molecule is a heterodimer comprised of structurally unrelated subunits, both of which are glycosylated. That this integrin, isolated from human epithelial cells, is novel was shown by DNA and amino acid sequence homologies. No obvious serologic cross reactivities were detected with other integrins. The $\beta$-chain of the epithelial integrin has a molecular weight which is significantly higher than other integrin $\beta$-chains. It is postulated that this is due to a large sialic acid content.

The interaction of cells with the extracellular matrix is important for the information, maintenance, and repair of tissues as well as for other biological processes such as the metastasis of cancer cells. This interaction is mediated, in part, by a family of cell surface receptors called integrins (Hynes, (1987) supra: Ruoslahti and Pierschbacher, (1987) supra; Buck and Horwitz, 1987, supra). These receptors form a link between the extracellular matrix and the cytoskeleton and may transmit signals from the extracellular to the intracellular environment that affect cell behavior.

Integrins are heterodimers comprised of $\alpha$ and $\beta$ subunits, that are noncovalently associated transmembrane glycoproteins. At least 11 $\alpha$ chains (Ruoslahti and Giancotti, (1989), supra) and 6 $\beta$ chains (Sheppard et al., (1990), supra) have been recognized in man. Each $\alpha$ subunit tends to associate with only one type of $\beta$ subunit, but there are several exceptions to this rule (Hemler et al., (1989) supra: Cheresh et al. (1989), supra; Holzmann et al., (1989) supra; Freed et al., (1989) supra).

Because integrin heterodimers are grouped into three families, based upon which of the three $\beta$-chains they contain, it is proposed that the $\beta$-chain of the present invention be designated $\beta_4$ in recognition of its defining a fourth integrin $\beta$-chain family. It has also been proposed that the $\alpha$ subunit of this integrin, which is primarily expressed on epithelial cells, be called $\alpha_E$ or $\alpha_6$. The alpha subunit, $\alpha_6$, also appears to associate with the $\beta_1$ integrin subunit. Disclosed herein is the complete cDNA nucleotide sequence and the deduced amino acid sequence of both the $\alpha_6$ and $\beta_4$ subunits. Although $\alpha_6$ and $\beta_4$ show some homology to other integrin $\alpha$ and $\beta$ chains, they surprisingly contain unique structural features having novel functional properties and applications.

Other features and advantages of the present invention will become apparent from the following detailed description which illustrates, by way of example, the principles of the invention.

BRIEF DESCRIPTION OF THE FIGURES

FIG. 1 is a photocopy of a two-dimensional gel of immunoprecipitates obtained by reacting HB 9318 with radiolabeled extracts of FG cells.

FIG. 2 is a photocopy of a two-dimension gel of immunoprecipitates obtained by reacting HB 9319 with radiolabeled extracts of FC cells.

Figure 6B:
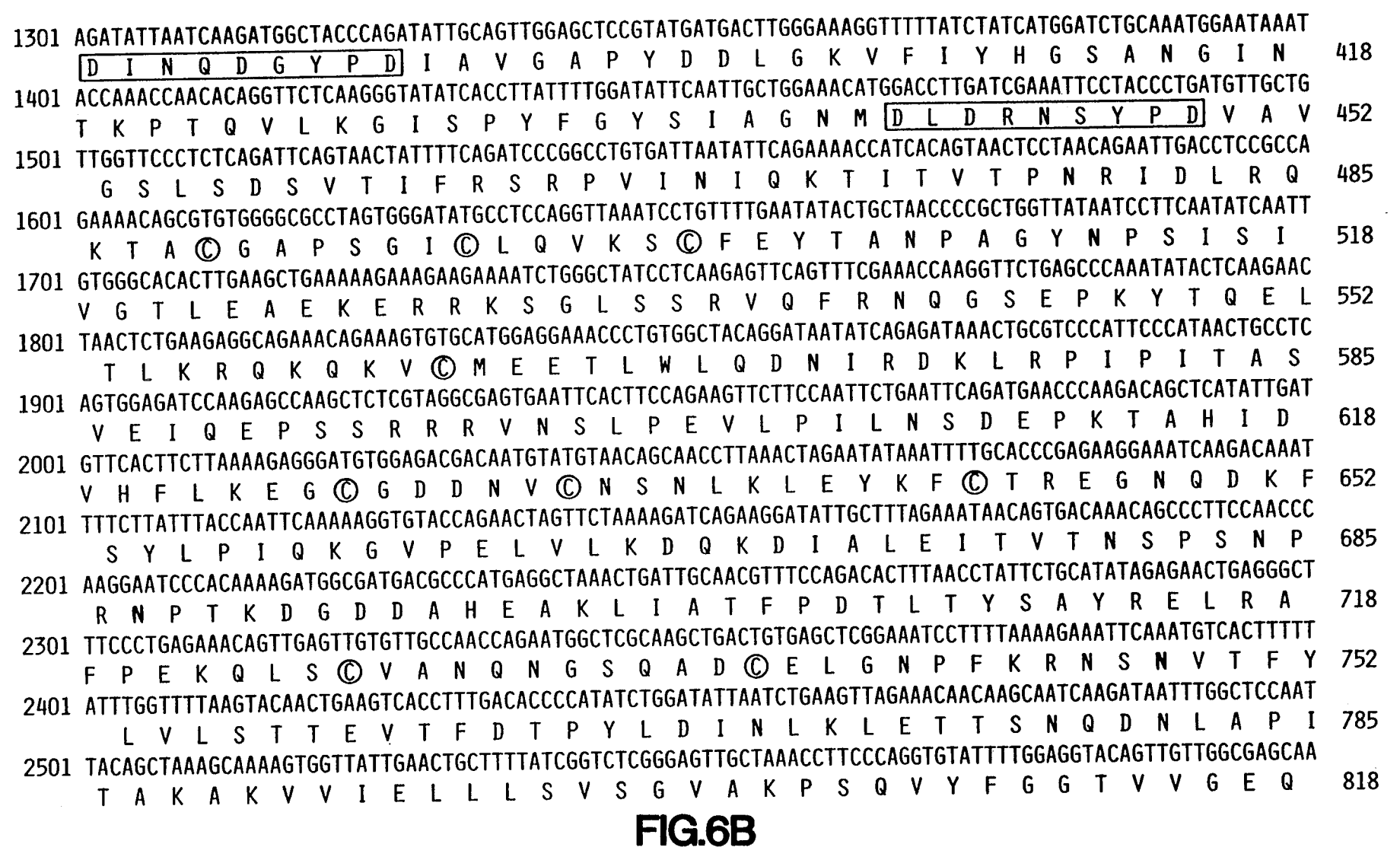
Figure 6C:
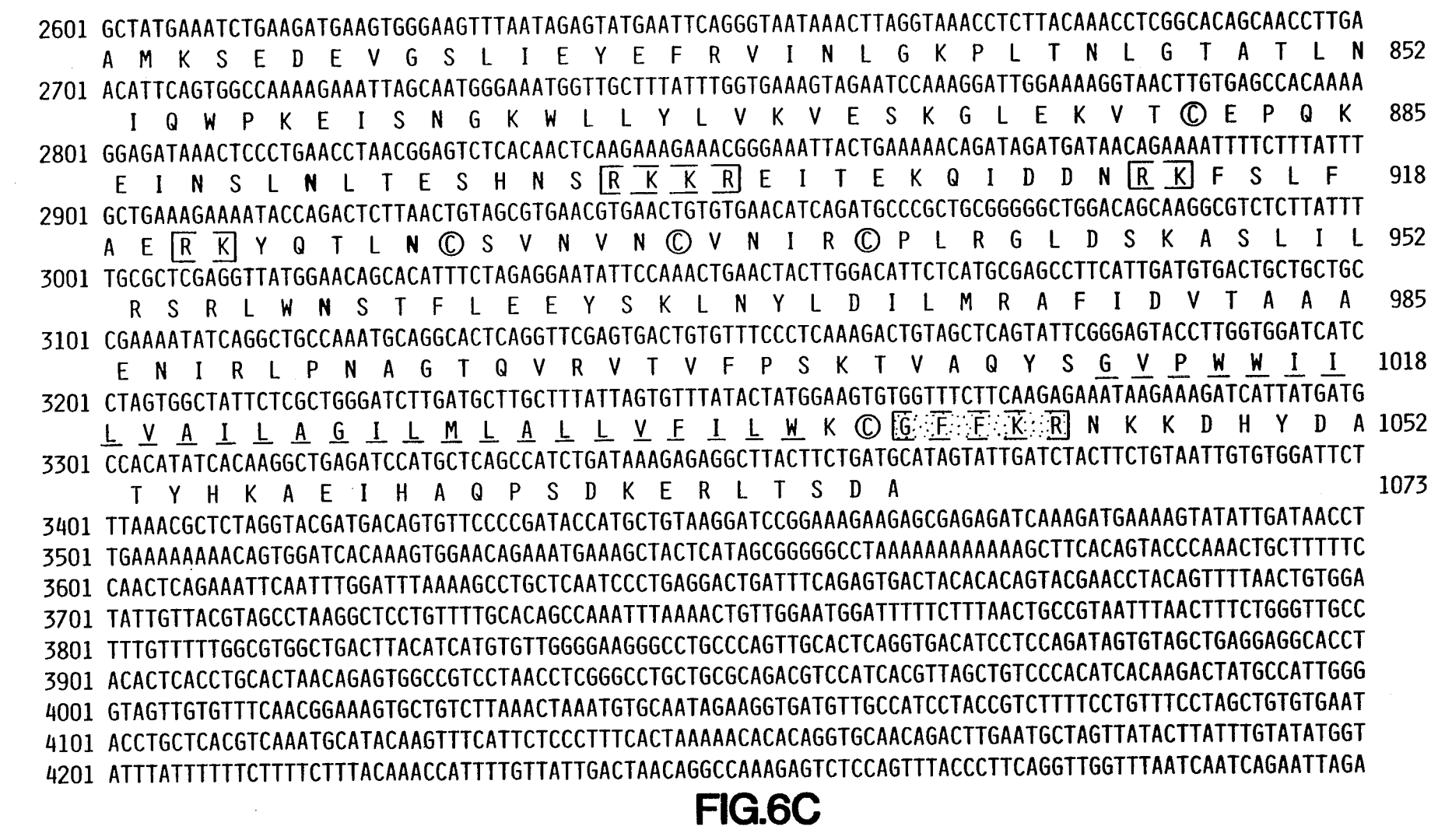

FIGS. 6A, 6B, 6C, and 6D are the typewritten nucleotide sequence and deduced amino acid sequence of the human $\alpha_6$ subunit.

FIGS. 8A and 8B are a typewritten, Partial nucleotide sequence and deduced amino acid sequence of the human $\beta_4$ subunit highlighting the regions where insertions occur, presumably based on alternative mRNA splicing.

FIGS. 9A, 9B, 9C, 9D and 9E are the typewritten nucleotide sequence and deduced amino acid sequence of the human $\beta_4$ subunit.

FIG. 11A is a diagram illustrating the location and expected size of PCR products; FIG. 11B is a photocopy of an autoradiogram of PCR products from various cDNAs.

FIGS. 12A–12G are photocopies of immunofluorescent staining of FG carcinoma cells.

DETAILED DESCRIPTION OF THE PREFERRED EMBODIMENT

I. DEFINITIONS

Figure 3A:
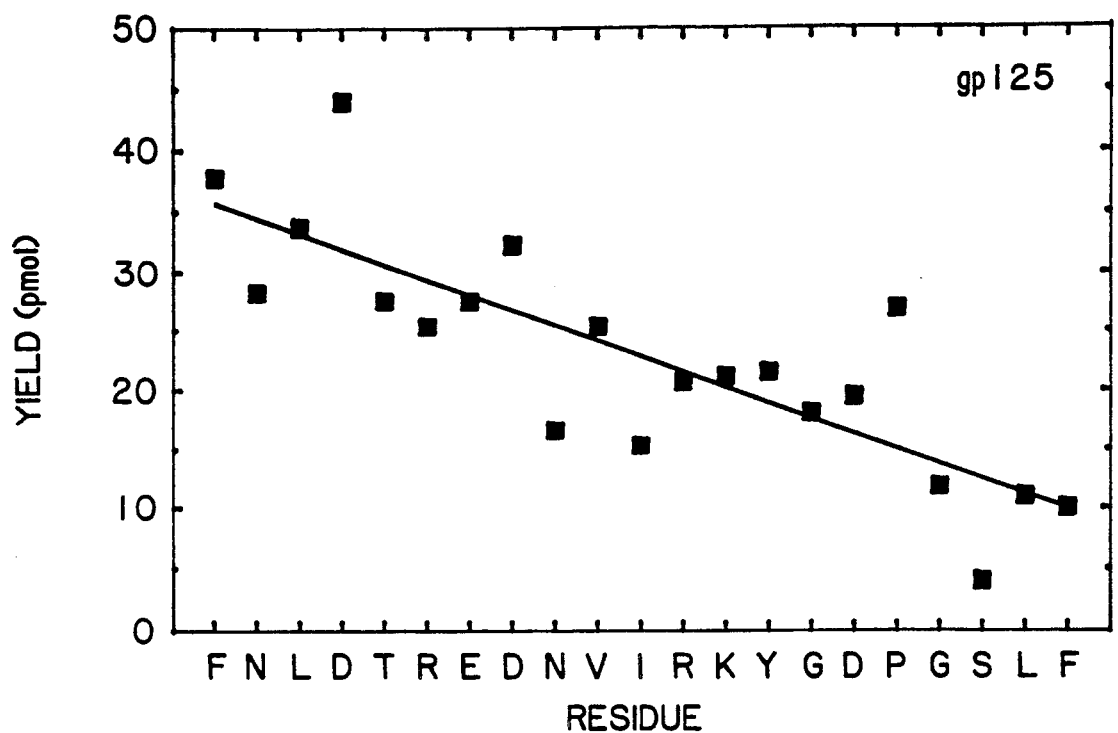
FIGS. 3A and 3B show amino acid residue sequences of $\alpha_6$ (gp125), and $\beta_4$ (gp150), purified using HB 9318.

"Monoclonal antibodies (Mabs) reactive with HPC" refers to homogenous populations of immunoglobulins which are capable of immunoreaction with antigens expressed on human pancreatic cancer (HPC) cells. It is understood that there may be a number of antigens present on the surface of any cell and, alternatively, that certain receptors present on HPC cells may also occur on other malignant or normal cell types. Moreover, such antigens may, in fact, have a number of antigenic determinants. The antibodies of the invention may be directed against one or more of these determinants. Any characteristic antigen associated with HPC may provide the requisite antigenic determinant.

Immunoglobulins, like all proteins, may exist in acidic, basic or neutral form depending on their amino acid composition and environment, and may be found in association with other molecules such as saccharides or lipids. The immunoglobulins of the present invention fall within the definition regardless of status in this regard as long as they remain capable of selectively reacting with HPC associated antigens.

"Cells" or "cell line" refers to the cells apparently denoted as well as the progeny thereof. It is known that during cell multiplication and growth, cells or cell lines may not remain precisely constant in their genetic makeup and the progeny may, indeed, be distinguishable in some way from the parent cells. So long as the cells referred to herein retain the characteristic of secretion capability for Mabs reactive with HPC, as defined above, they are to be considered included in the definition.

"Immortalizing cell line" refers to a cell line which can be maintained perpetually, for practical purposes, in cell culture, i.e., for an indefinite number of transfers. It must also, when fused to an ordinary non-transformed cell line, which would normally not survive for more than a few days or weeks as a unicellular culture, be able to confer on the fusion product its own immortal properties.

A sequence is "substantially homologous" when it is at least about 40 per cent homologous, preferably at least about 50 per cent homologous.

II. HYBRIDOMA PREPARATION

A. GENERAL DESCRIPTION OF HYBRIDOMA PREPARATION

The examples below describe the preparation of specific hybridoma cell lines producing monoclonal antibodies reactive with HPC cell antigens. It will be appreciated, however, that alternative methods may be employed to obtain alternative embodiments of the specific Mabs reactive with HPC cell antigens.

Techniques for preparing hybridomas are generally well-known in the art. Generally speaking, such hybridoma cell lines are prepared by a process involving the fusion under appropriate conditions of an immortalizing cell line and a B lymphocyte cell line appropriately immunized to produce the desired antibody. While the immortalizing cell lines so used are often of murine origin, those of any other mammalian species may be employed alternatively including those of rat, bovine, canine, human origin and the like. The immortalizing cell lines are most often of tumor origin, particularly myeloma cells, but may also include normal cells transformed with, for example, Epstein Barr Virus. Any immortalizing cell here may be used to prepare the hybridomas of the present invention.

Cells capable of secreting antibodies were employed as fusion partners, such as spleen cells or peripheral blood lymphocytes. The animal from which the cells were to be derived was immunized at intervals with whole cell suspensions of human pancreatic cancer cells. Alternatively, cell extracts or purified antigen may be used for immunization.

The immortalizing cells and lymphoid cells were fused to form hybridomas according to standard and well known techniques employing polyethylene glycol as a fusing agent. Alternatively fusion may be accomplished by electrofusion. Hybridomas are screened for appropriate monoclonal antibody secretion by assaying the supernatant or protein purified from the ascites for reactivity with the desired cell or antigen. Such assay techniques include, among others, ELISA, RIA Western Blotting, or immunoprecipitation.

In the present invention, hybridomas were initially screened for production of antibodies reactive with HPC cells. Alternatively, HPC cell extracts or purified antigens could be used for screening. In order to further characterize the monoclonal antibodies, their reactivity with various HPC cell lines, other tumor cell lines and a variety of other normal, malignant and non malignant pathological human tissues was determined using standard assay techniques such as ELISA, RIA, immunoprecipitation, histochemical staining procedures including indirect immunoperoxidase or indirect immunofluorescence staining. The hybridomas of the present invention were found to produce monoclonal antibodies generally highly reactive with all human pancreatic cell lines. They also displayed high reactivity with cells derived from other tumors, noticeably those of gastrointestinal and genitourinary tract origin. Moreover, although they displayed some reactivity with certain normal tissues, the Mab displayed negligible reactivity with major organs such as liver and kidney. Apparently, the antigens against which the antibodies are directed are highly expressed on HPC cells but only moderately or less on other cell types.

Because of their selective reactivity with HPC cell derived antigens the monoclonal antibodies are useful for both diagnosis and therapy of HPC and other carcinomas. Moreover, their non-reactivity with liver and kidney cells in particular permits them to be used therapeutically with relatively little risk of targeting these critical organs.

The antibodies of the invention are also useful in the preparation of cell surface markers reactive with them using immunoprecipitation and/or affinity chromatography of cell membrane preparations. The marker reactive with HB 9318 antibodies described below is a member of the integrin super family, and is functional in mediating binding to the extracellular matrix. Accordingly, this marker is involved in metastasis and colonization of malignant cells.

B. PARTICULAR HYBRIDOMA EMBODIMENTS

The following examples illustrate a method for preparing hybridomas which can serve as sources for the desired monoclonal antibodies, and the antibodies thus produced. While the methods described are typical of those which might be advantageously used, other alternative procedures known to those skilled in the art may be alternatively employed. The examples are thus intended to illustrate, but not to limit the invention.

EXAMPLE 1

PREPARATION OF HYBRIDOMA CELL LINE

Murine Mabs reactive with HPC cell lines were produced essentially according to the standard techniques of Kohler and Milstein, Nature 256:495 (1975). Briefly, standard HPC cell lines such as COLO 357 and its subclones were used to obtain the antigenic preparation. Preferably cells of the cell line termed FG were employed. (Kajiji, S. M., Intraneoplastic Diversity in Human Pancreatic Cancer, Ph.D. Thesis, Brown University (1984). Alternatively other pancreatic cell lines expressing the antigens may be used, such as BxPC-3 (ATCC No. CRL1687). The cells were grown in a monolayer culture and harvested by EDTA treatment. Briefly, confluent monolayers were incubated for 20 minutes at 37° C. with PBS containing 10 mM EDTA and 0.02% KCl. The detached cells were collected, centrifuged at 1000 x g for 10 minutes and washed twice with cold PBS. Alternatively, cell suspensions were derived from FG xenografts grown in Balb/c thymic nude mice.

Two to four month old normal Balb/c mice were immunized with whole cell suspensions at weekly intervals with six intraperitoneal 0.5 ml injections, containing approximately $5 \times 10^6$ to $5 \times 10^8$ cells/injection/mouse. Three days after the final injection, the mice were sacrificed and the spleens removed. The spleens were placed in serum free Dulbecco's Minimal Essential Medium (DMEM) in separate Petri dishes and washed. The splenocytes were gently teased out of the fibrous splenic capsule using a rubber policeman. The cell suspension was then placed in a 15 ml tube and centrifuged at 1000 x g for 10 minutes. The pellet was then washed twice with serum free DMEM.

The washed spleen cells and the P3X63Ag8 myeloma cells were fused according to the method of Kohler and Milstein, supra. The immortalized cell line fusion partners used were the murine myeloma cell line P3X63Ag8 (ATCC Accession No. TIB9) These myeloma cells were grown at a density of $5 \times 10^5$ cells/ml and harvested by centrifugation at 1000 x g for 10 minutes. The cell pellet was washed twice with serum free DMEM. Finally, the spleen cells and the P3X63Ag8 myeloma cells were combined at a ratio of 7:1 in a 50 ml tube and pelleted by centrifugation (1000 g for 10 minutes). The pellet was gently loosened and 1 ml of a 35% polyethylene glycol (PEG) solution was gently bubbled over the cells. After 1 minute, 1 ml of DMEM, containing 10% fetal calf serum (FCS) (Gibco, Grand Island, N.Y.) was added to the cell suspension and gently mixed.

The PEG was subsequently diluted by the addition of 10 ml DMEM containing 10% FCS and the cells were repelleted. The cell pellet containing hybridoma fusion products was resuspended in 30 ml hypoxanthine aminopterin-thymidine (HAT) medium (aminopterin from Sigma Chemical Co., St. Louis, Mo.; hypoxanthine and thymidine from Calbiochem, La Jolla, Calif.).

This cell suspension was then combined with 400 ml of HAT medium containing $2 \times 10^6$ thymocytes per ml (feeder cells). The contents were distributed into sterile 96 well plates (Costar, Cambridge, Mass.) and placed immediately in an incubator at 37° C. The spent media was replaced with fresh thymocyte-containing HAT media after one week. Using this type of protocol, successful hybridoma cultures were obtained which could be maintained with periodic addition of fresh DMEM containing 10% FCS.

Hybridomas producing monoclonal antibodies reactive with HPC cells were selected. After the cultures reached a cell density that covered 75-100% of the microliter well surface, media from the hybridomas were screened for the presence of anti-HPC antibody, using a standard ELISA protocol. (Schultz, Cancer Res. 44:5914(1984)). Briefly, tumor cells dried onto the bottom of 96-well miniplates (Dynatech Microliter Plates, American Scientific Products, McGaw Park, Ill.) were used as targets. The wells of antigen-coated 96 well plates to be used were rinsed with buffer A pH 8.0 (20 mM Tris, containing 150 mM NaCl, 0.2% Tween 20 and 0.01% Thimerosal). The hybridoma supernatant diluted 1:2 in buffer B (buffer A containing 0.1% bovine serum albumin) was added to the wells and incubated for 1 hour at room temperature to permit binding of specific antibodies. Specifically bound antibodies were detected by adding horseradish peroxidase-conjugated rabbit anti-mouse immunoglobulin (BioRad, Richmond, Calif.) to wells that were rinsed free of the excess hybridoma supernatant by washing with buffer A. After incubation for 1 hour at room temperature the secondary antibody was decanted, the wells washed with buffer A, and 50 ml/well of substrate solution (ten milliliters of 80 mM citrate phosphate buffer, pH 5.0 containing 4 mg 0-phenylenediamine (Sigma Chem. Co., St. Louis, Mo.) and 4 ml 30% hydrogen peroxide) was added. The plates were incubated in the dark for 30 min at RT and the color reaction was stopped by adding 25 ml of 4M sulfuric acid to each well. Specifically bound antibodies were detected by measuring the absorbance at OD 490 on an ELISA scanner C model EL310, Biotek Instruments Winooski, Vt.) within 30 min. Reactivity was graded as follows: $A_{490}F0.15$, —; $A_{490}=0.15$ to 0.3, 1+; $A_{490}=0.3$ to 0.6, 2+; $A_{490}=0.6$ to 1.2, 3+; $A_{490}fl.2$, 4+. Hybridomas that were reactive with the immunizing FG cells but not with the lymphoblastoid 721-P cells were further screened for reactivity with frozen sections of HPC according to the procedure of Example 2 below. Only those that were reactive with frozen sections of HPC but not reactive with frozen sections of normal human liver, kidney and lung were selected. The two hybridoma cells lines selected for further study were designated HB 9318 and HB 9319, respectively.

III. CHARACTERIZATION OF MONOCLONAL REACTIVITY

EXAMPLE 2

A. REACTIVITY WITH HUMAN TUMOR TISSUES

The reactivity of the monoclonal antibodies was determined by indirect immunoperoxidase staining as follows. Two- to 4-mm sections of frozen tissue blocks were cut on a cryotome, mounted on gelatin-coated glass slides, air-dried, and tested immediately in an indirect immunoperoxidase assay using the method of Taylor, Arch. Pathol. Lab. Med. 102:113 (1970). Briefly, after washing once in Hanks' balanced salt solution (Gibco, Grand Island, N.Y.) and phosphate buffered saline (PBS 10 mM sodium phosphate, 0.15M Nacl, pH 7.0), sections were incubated at room temperature sequentially with: diluting buffer (PBS containing 5% normal goat serum and 1% bovine serum albumin) for 15 min; a 1:2 dilution of hybridoma supernatants or appropriate isotype-matched controls for one hour; horseradish peroxidase-conjugated goat anti-mouse Ig antiserum (Bio-Rad, Richmond, Calif.) diluted 1:50 and containing 5% normal human serum for one hour; and finally substrate buffer (10 mM Tris, pH 7.4, 0.6 mg/ml 3,3'-diaminobenzidine, 0.015% $H_2O_2$) for 15 min. Washes with HBSS and PBS were performed between incubations. Sections were counterstained in 1% methylene blue, dehydrated through graded ethanol, washed in Histo-Clear (National Diagnostics, Somerville, N.J.), mounted in Pro-Texx (Lerner Laboratories, New Haven, Ct.), and examined by light microscopy.

Table 1 summarizes the reactivity of monoclonal antibodies produced by hybridoma cell lines HB 9318 and HB 9319 with 65 different tumors. HB 9318 was generally reactive only with carcinomas of the pancreas gastro-intestinal tract, genitourinary tract, and head and neck tumors. Moreover, in virtually all instances, staining by the HB 9318 Mabs was distinctly associated with the basement membranes surrounding tumor foci, producing a characteristic one-sided basal surface staining of cells at the epithelial stromal interface. In the few cases of lung carcinomas, melanoma and breast cancer tissues that were stained, reactivity was also confined to the basement membranes.

Mab HB 9319 reacted with each of the seven pancreatic adenocarcinomas tested, including pancreatic carcinoma of the acinar cell type. Mab HB 9319 displayed a wide range of reactivity among tumor tissues examined. Moreover, reactivity of HB 9319 was generally intense with the majority of tumor cells within a tissue. Tumor cell basement membranes were also stained in some cases.

TABLE 1

REACTIVITY OF MONOCLONAL ANTIBODIES WITH FRESH FROZEN HUMAN TUMOR TISSUE SECTIONS BY IMMUNOPEROXIDASE STAINING[a]

|  | HB 9318 | HB 9319 |
|---|---|---|
| Pancreatic Cancer | | |
| ductal adenocarcinoma | —[b] | 2+ |
| | 2+[b] | 1+ |
| | 2+[b] | 4+ |
| | — | 1 |
| | 4+[b] | 1+ |
| | 3+[b] | 3+ |
| | 4+ | 4+ |
| islet cell Cancer/ | — | — |
| insulinoma | — | 1+ |
| acinar cell Cancer | — | 3+ |
| Oral Squamous Cancer | 1[b] | 3+ |
| | 1[b] | 4+ |
| | — | 2+ |
| | —[b] | 4+ |
| Adenoid Cystic Cancer | 3+ | 2+ |
| Salivary Gland Cancer | 4+[b] | 3+ |
| Esophageal Cancer | 3+[b] | 3+ |
| Gastric Cancer | 3+[b] | 3+ |
| | 2+ | 4+ |
| | 3+ | 3+ |
| | 1+[b] | 3+ |
| Colon Cancer | 3+[b] | 3+ |
| | —[b] | 1+ |
| | 3+ | 3+ |
| | 3+[b] | 4+ |
| Hepatoma | — | 2+ |
| | — | 2+ |
| Laryngeal Cancer | 2+[b] | 4+ |
| | 2+[b] | 3+[b] |
| Melanoma | 1+[b] | 4+ |
| | — | 4+ |
| | — | 4+ |
| Sarcoma | — | 4+ |
| | — | 4+ |
| Lung Cancer | | |
| adenocarcinoma | 1+ | 1+ |
| | — | 3+ |
| | — | 1+ |
| squamous Cancer | 1+[b] | 3+ |
| | — | 2+ |
| | — | 3+ |
| | — | 3+ |
| | — | 3+ |
| adenosquamous | 1+[b] | 3+ |
| oat cell Cancer | — | — |
| | — | — |
| large cell Cancer | 4+ | 4+ |
| mesothelioma | — | 1+ |
| Breast Cancer | — | 3+ |
| | — | 4+ |
| | — | 3+ |
| | — | 2+ |
| | 1+ | 2+ |
| Cervical Cancer | 2+[b] | 1+ |
| | 1+ | 4+ |
| Endometrial Cancer | — | 3+ |
| | — | 4+ |
| | 3+[b] | 2+ |
| Ovarian Cancer | — | 4+ |
| | — | 3+ |
| | 3+[b] | 2+ |
| Prostatic Cancer | 1+[b] | 4+ |
| Bladder Cancer | 1+[b] | 2+ |
| | 3+[b] | 2+[b] |
| Kidney Cancer | — | 4+ |
| | 2+ | — |

[a]Intensity of staining was scored from "1+" to "4+," with 4+ indicating greatest intensity and with "—" indicating lack of staining.
[b]Basement membrane staining.

B. REACTIVITY WITH HUMAN CELL LINES

The reactivity of Mabs against a panel of cell lines in culture was determined by ELISA reactivity, according to the Method of Schultz (1984), Cancer Res. 44:5914, as detailed in Example 1.

Cells dried onto the bottom of 96-well miniplates were used as targets for ELISA. Horseradish peroxidase-conjugated goat anti-mouse Ig antiserum (Bio Rad, Richmond, Calif.) was used as the secondary antibody.

The reactivity of Mabs HB 9318 and HB 9319 is shown in Table 2. Both Mabs were reactive with the majority of the ten HPC cell lines tested. Moreover, both displayed particularly strong reactivity with cell lines derived from lung cancer, skin cancer and gastrointestinal and genitourinary tract tumors. HB 9319 displayed moderate to strong positivity with tumor cell lines of neuroectodermal origin including melanoma, glioblastoma and neuroblastoma lines. Both antibodies were generally non-reactive with human red blood cells of blood types AB+, A+, B+, O+, and O−, normal diploid fibroblasts and leukemic or lymphoid cell lines.

TABLE 2

ELISA REACTIVITY OF MONOCLONAL ANTIBODIES WITH CULTURED HUMAN CELLS

| Cell lines (ATCC NO.) | HB 9318 | HB 9319 |
|---|---|---|
| Pancreatic Cancer | | |
| Colo 357[a] | 3+ | 2+ |
| FG[a] | 3+ | 3+ |
| SG[a] | 3+ | 3+ |
| FG-Met-2[a] | 4+ | 4+ |
| RWP-1[a] | 4+ | 2+ |
| RWP-2[a] | 3+ | 1+ |
| PANC-1 (CRL 1469) | 3+ | 3+ |
| ASPC-1 (CRL 1682) | 3+ | 1+ |
| Hs 766T (HTB 134) | 4+ | 1+ |
| BxPC-3 (CRL 1687) | 4+ | 4+ |
| Lung Cancer | | |
| adenocarcinoma | | |
| UCLA-P3[b] | — | 2+ |
| A549 (CCL 185) | 2+ | 1+ |
| CALU 6 (HTB 56) | — | 4+ |
| squamous cancer | | |
| T-222[b] | 2+ | 4+ |
| SK-MES-1 (HTB 58) | 3+ | 3+ |
| CALU-1 (HTB 54) | 2+ | 3+ |
| USCLS-1[b] | 3+ | 3+ |
| oat cell Cancer | | |
| T-293[c] | — | 1+ |
| NCI-H69 (HTB 119) | — | — |
| Breast Cancer | | |
| 734B[d] | — | 3+ |
| BT-20 (HTB 19) | 3+ | 4+ |
| MDA-MB-4³⁵S (HTB 129) | — | 3+ |
| Bladder Cancer | | |
| T24 (HTB 4) | — | 2+ |
| J82 (HTB 1) | — | 2+ |
| 5637 (HTB 9) | 2+ | 3+ |
| Cervical Cancer | | |
| ME-180 (HTB 33) | 3+ | 4+ |
| Prostatic Cancer | | |
| DU-145 (HTB 43) | 2+ | 3+ |
| Pharyngeal Cancer | | |
| FaDu (HTB 43) | 3+ | 4+ |
| Skin Cancer | | |
| A-431 (CRL 1555) | 3+ | 3+ |
| Colon Cancer | | |
| COLO 396[d] | 4+ | 4+ |
| Hepatoma | | |
| SK-HEP-1 (HTB 52) | 3+ | 2+ |
| Mesodermal Tumor | | |
| SK-UT 1 (HTB 114) | — | 2+ |
| Melanoma | | |
| ML-873-1[c] | — | 2+ |
| WM239A[c] | — | 3+ |
| WM2664 (CRL 1676) | — | 3+ |
| A-375P[c] | — | 4+ |
| A-375M[c] | — | 3+ |
| M14[c] | — | 3+ |
| M21[c] | — | 4+ |
| MS-1[c] | — | 3+ |
| FOSS[c] | — | 3+ |
| Melur[c] | — | 3+ |
| Glioblastoma | | |
| U38MG (HTB 16) | — | 1+ |
| U87MG (HTB 14) | — | 3+ |
| U-373MG (HTB 17) | — | 3+ |
| Neuroblastoma | | |

TABLE 2-continued

ELISA REACTIVITY OF MONOCLONAL ANTIBODIES WITH CULTURED HUMAN CELLS

| Cell lines (ATCC NO.) | HB 9318 | HB 9319 |
|---|---|---|
| SK-N-SH (HTB 11) | — | 2+ |
| SK-N-MC (HTB 10) | — | — |
| LAN-1[c] | 2+ | 1+ |
| B-Lymphoblastoid | | |
| L14[b] | — | 1+ |
| LG-2[b] | — | 1+ |
| 721-p[e] | — | — |
| GM3107[b] | — | 2+ |
| T-Lymphoblastoid | | |
| MOLT-4 (CRL 1582) | — | — |
| HPB-ALL[b] | — | 2+ |
| HSB-2[d] | — | — |
| Promyelocytic Leukemia | | |
| HL-60 (CCL 240) | — | — |
| Erythroleukemia | | |
| K562 (CCL 243) | — | — |
| Diploid Fibroblast | | |
| WI-38 (CCL 75) | — | — |
| Human RBC | — | — |

Cell lines were obtained as follows:
[a]P. Meitner, Department of Medicine, Brown University
[b]L. Walker, Department of Immunology, Scripps Clinic and Research Foundation
[c]R. Reisfeld, Department of Immunology, Scripps Clinic and Research Foundation
[d]T. Edginton, Department of Immunology, Scripps Clinic and Research Foundation
[e]F. Bach, University of Minnesota.

C. REACTIVITY WITH NON-MALIGNANT PATHOLOGIC HUMAN TISSUES

The reactivity of the Mabs with a panel of inflammatory pancreases, benign tumor and hyperplastic epithelia was determined by indirect immunoperoxidase staining of frozen tissue sections, according to the method of section A, above. Both Mab HB 9318 and Mab HB 9319 showed some reactivity with the duct cells of chronic pancreatitis tissues. Mab HB 9319 was widely reactive in that it stained every non-maligant pathologic tissue examined, although always in discrete areas. Table 3 shows the results of testing with this panel of tissues.

TABLE 3

REACTIVITY OF MONOCLONAL ANTIBODIES WITH FRESH FROZEN NON-MALIGNANT PATHOLOGIC HUMAN TISSUE SECTIONS BY IMMUNOPEROXIDASE STAINING

| Cell Lines (ATCC No.) | HB 9318 | HB 9319 |
|---|---|---|
| Pancreas (chronic pancreatitis) | | |
| acini | — — | — — |
| ducts | 2+ —[b] | 2+ 1+ |
| islets of Langerhans | — — | — — |
| Pancreas (SLE)[a] | | |
| acini | — | 4+ |
| ducts | —[b] | — |
| islets of Langerhans | — | — |
| Uterus (leiomyoma) | — — — — | 3+ 4+ 4+ 4+ |
| Ovary (fibroadenoma) | — | 2+ |
| Endometrium (hyperplastic) | 3+ | 4+ |
| Prostate (hyperplastic) | | |
| upper layers of epithelium | — | 3+ |
| basal layers of epithelium | 4+ | 3+ |
| basement membrane | 4+ | — |

[a]SLE - Systemic Lupus Erythematosus
[b]Basement Membrane Staining

D. REACTIVITY WITH NORMAL ADULT AND FETAL TISSUES.

The reactivity of the Mabs with fresh frozen normal adult and fetal tissues was determined by indirect immunoperoxidase staining according to the method of section A, above. The antibodies were unreactive with the vast majority of normal tissues examined.

Mab HB 9318 displayed some reactivity with the basal epithelial layers or basement membranes of the esophagus, cervix, and large intestine, plantar skin, breast tissue and ileal epithelium. The restricted expression of the HB 9318 antigen by the proliferating cell layers of normal stratified epithelia and its localization at the epithelial stromal interface suggests that this molecule may be an early differentiation antigen (possibly involved in cell adhesion) of epithelial cells that is re-expressed following malignant transformation. Further, the HB 9318 antigen may be useful for diagnosis and therapeutic intervention of other skin-related disorders such as psoriasis and basal cell carcinomas and may prove to be a valuable cell surface marker for investigating epidermal cell biology.

Mab HB 9319 reacted with the acinar cells of adult and fetal pancreases, fetal pancreatic ducts, and the parenchyma and bile ducts of ⅓ livers that were tested. It was moderately reactive with the esophagus, stomach and small intestine, cervix, uterus, breast, fetal and adult lung parenchyma, fetal kidney, cerebral cortex, and with the molecular layers and Purkinje cells within the adult cerebellum. All layers of plantar skin including basement membrane were also intensely stained.

Table 4 summarizes the results of this panel of tests.

TABLE 4
REACTIVITY OF MONOCLONAL ANTIBODIES WITH FRESH FROZEN NORMAL HUMAN TISSUE SECTIONS BY IMMUNOPEROXIDASE STAINING

| | HB 9318 | HB 9319 |
|---|---|---|
| Esophagus | | |
| *stratified squamous epithelium* | | |
| upper layers | — | 3+ |
| basal layers | 4+ | 4+ |
| basement membrane | 4+ | — |
| Stomach | | |
| gastric pits | — | 3+ |
| *gastric glands* | | |
| parietal cells | — | 2+ |
| chief cells | — | 2+ |
| lamina propria | — | 1+ |
| Small Intestine | | |
| jejunal epithelium | — | 2+ |
| ileal epithelium | 3+ | 3+ |
| basement membrane | 4+ | — |
| Large Intestine | | |
| colonic epithelium | — | 1+ |
| crypts of Lieberkuhn | — | 1+ |
| basement membrane | 4+ | — |
| lamina propria | — | 1+ |
| Liver | | |
| parenchyma | — — — | — 3+ — |
| bile ducts | — 1+ — | — 3+ — |
| Pancreas (adult) | | |
| acini | — — — — | 4+ 4+ |
| ducts | — — —a — | — — — — |
| islets of Langerhans | — — — — | — — — — |
| Pancreas (fetal) | | |
| acini | — | 4+ |
| ducts | —a | 4+ |
| islets of Langerhans | — | — |
| Thymus | | |
| cortex | — | — |
| medulla | — | — |
| Lymph Node | | |
| nodules | — | — |
| germinal centers | — | 1+ |
| Spleen | | |
| white pulp | — | — |
| red pulp | — | 1+ 1+ |
| Kidney (adult) | | |
| glomeruli | — — — | — — — |
| proximal tubules | — — — | — — — |
| distal tubules | — — — | — — — |
| Kidney (fetal) | | |
| glomeruli | — | 3+ |
| proximal tubules | 1+ | 3+ |
| distal tubules | — | 3+ |
| Cervix | | |
| columnar epithelium | — 1+ | 4+ 3+ |
| basement membrane | 4+ 4+ | — — |
| *squamous epithelium* | | |
| upper layers | — — | 3+ 3+ |
| basal layers | 4+ 4+ | 4+ 4+ |
| basement membrane | 4+ 4+ | — — |
| Uterus | | |
| endometrium | 1+ — | 3+ 2+ |
| myometrium | — — | 4+ 2+ |
| Ovary | | |
| cortex | — | — |
| medulla | — | — |
| Breast | | |
| lobule | 4+ 2+ | 4+ 4+ |
| duct | 4+ 3+ | 4+ 4+ |
| basement membrane | 4+ 4+ | 4+ 4+ |
| Lung (adult) | | |
| parenchyma | — — — — | 2+ 2+ — |
| Lung (fetal) | | |
| parenchyma | — | 3+ |
| Thyroid | | |
| epithelial cells | — | 1+ |
| colloid | — | — |
| Cerebrum | | |
| cortex | — | 3+ |
| Cerebellum | | |
| granular layer | — | — |
| molecular layer | — | 2+ |
| Purkinje cells | — | 2+ |
| Plantar skin | | |
| stratum corneum | — | 3+ |
| stratum granulosum | — | 3+ |
| stratum spinosum | 1+ | 3+ |
| stratum germinativum | 3+ | 4+ |
| basement membrane | 4+ | 4+ | aBasement membrane staining

E. REACTIVITY WITH CELL SURFACES

To determine whether the antigens recognized by the Mabs were expressed on surface of cells of reactive tissues, viable HPC cells were tested with the Mabs in indirect immunofluorescence assays as follows:

Indirect Immunofluorescence Staining

Cells grown to confluence on glass cover slips were washed once with cold HBSS, overlaid with 0.1 ml of 1:2 hybridoma supernatant for one hour at 4° C., washed in cold HBSS, and overlaid with 0.1 ml of 1:50 fluorescein isothiocyanate-conjugated goat anti mouse Ig antiserum (Tago, Burlingame, Calif.) for one hour at 4° C. After washing and fixing in 3% paraformaldehyde, cells were mounted in 80% glycerol, 1 mg/ml p-phenylenediamine, 200 mM Tris, pH 8.5, examined and photographed with a Zeiss fluorescence microscope.

Both Mab HB 9318 and HB 9319 showed distinct staining of the plasma membrane, indicating recognition of cell surface structures. Both stained the entire cell population, displaying a contiguous, linear membrane pattern.

IV. ANTIGEN CHARACTERIZATION

EXAMPLE 3

IMMUNOCHEMICAL CHARACTERIZATION OF ANTIGENS

In order to assess the chemical nature of the antigens recognized by Mabs, HPC cells were radiolabeled by incubation with either L-[$^3$H] leucine or [$^3$H] glucosamine, detergent solubilized and then subjected to immunoprecipitation with Mab immunosorbents, as follows:

Ten ml of a 10% suspension of protein-A Sepharose (Pharmacia, Uppsala, Sweden) were incubated at 4° C. for 1 hour with 5 ml of rabbit anti-mouse Ig antibodies (Accurate Chemicals, Westbury, N.Y.) in 0.3 ml of PORT buffer (10 mM Tris, pH 8.5, 0.15M NaCl, 0.5% Tween 20, 0.1% Renex 30, 2.5 mM sodium azide, 0.1% ovalbumin). After washing twice with PORT buffer, incubating 1 hour at 4° C. with 1 ml hybridoma supernatants and washing twice with PORT buffer, the beads were incubated overnight at 4° C. with radiolabeled cell extract (1-2×10$^7$ cpm). The immunosorbents were washed 8 times with PORT buffer (10 mM Tris, pH 8.5, 0.15M NaCl, 0.5% Tween 20, 0.1% Renex 30, 2.5 mM sodium azide) and bound antigens were eluted in Laemmli buffer (Nature 227:680 (1970)). The samples were analyzed by SDS-PAGE on slab gels and visualized by fluorography.

Initial results of the SDS-PAGE analysis indicated that Mab HB 9318 recognized a doublet protein antigen, of 205 kd and 135 kd, respectively. Both bands were glycosylated as they incorporated [$^3$H]-glucosamine. In some cases two additional bands of 150 kd and 185 kd were also seen. A band of 116 kd co-precipitated with HB 9318 bands, but was non-specific since it could be removed by preabsorption with control immunosorbants. Mab HB 9319 recognized a highly glycosylated 140 kd protein.

Immunoprecipitation of a metabolically labeled HPC indicated that the antigenic determinants recognized by each of the monoclonals are carried by protein molecules. These proteins are also glycosylated, so that it remains to be determined whether the recognized epitopes are expressed by the protein or the glycan part of these molecules.

EXAMPLE 4

Characteristics of HB 9318 Antigen

Characterization of the antigen which immunoprecipitates with HB 9318 demonstrates that it is a two-chain heterodimer which is a member of the integrin class of cell adhesion receptors.

Integrins are heterodimers comprised of noncovalently associated transmembrane glycoproteins. (Reviews of the characteristics of integrins have been published by Hynes, R. O., *Cell* (1987) 48:549-554; Ruoslahti, E., et al, *Science* (1987) 238:491-497; and Buck, C. A. & Horwitz, A. F. (1987) *Ann. Rev. Cell. Biol.* 3:179-205.) The α-chains have high degrees of homology and the differences in the β-chain serve to place the various integrins into subfamilies. Integrin heterodimers are grouped into three families, based on which of the three β-chains ($\beta_1$, $\beta_2$ or $\beta_3$) they contain. The integrin of the present invention is believed to represent a fourth member of the integrin family because of its structurally distinct β-chain.

The integrin class of cell surface adhesion receptors is distinct from another type designated CAMs which are monomers which use polysialylation as a control element. The integrin to which HB 9318 binds is distinguished from other known integrins by its polysialylation. The designation of $\alpha_E\beta_4$ had been proposed as a designation for this novel integrin; but the designation $\alpha_6\beta_4$ is preferred.

The HB 9318 antigen contains two non-covalently bound glycopeptides, designated herein gp205 and gp125. The gp125 represents an analog to the α-chains of other integrins, the gp205 peptide is somewhat analogous to other integrin β-chains. This two-chain antigen has been shown by immunoperoxidase staining to be expressed only on the basolateral surfaces of the germinativa layer of epithelial cells while cells from the prickle-cell layer outwards were progressively devoid of reactivity. The integrin is evidently involved in cell adhesion.

When HB 9318 monoclonal antibody is used to immunoprecipitate pancreatic cancer cell lysates gp125 and gp205 are precipitated. When HB 9318 monoclonal antibody is used to immunoprecipitate placental cell lysates, gp125 is again precipitated, however a second gp150 B-subunit is precipitated. This gp150 appears to be structurally related to the gp205 β-subunit present in pancreatic cancer, with the exception that it is not as glycosylated.

A. DISTRIBUTION OF THE ANTIGEN AND α- AND β-CHAINS

Immunohistology of human epidermal sections with HB 9318 shows that staining is concentrated near the basement membrane and basolateral cell surfaces of the germinative layer. Upper cell layers are progressively devoid of reactivity. Thus its expression is restricted to this particular portion of the cell surface.

FG-met2 pancreatic carcinoma cells were used as test substrates; lung adenocarcinoma lines and short term normal human keratinocyte cultures gave identical results.

Cultures of FG-met2 pancreatic carcinoma cells were surface radioiodinated using $^{125}$I sodium iodide in standard protocols. Detergent lysates of these labeled cells were immunoprecipitated with HB 9318, and the immunoprecipitate applied to polyacrylamide gels under reducing and non-reducing conditions. Under reducing conditions, a 205 kd band was detected; under non-reducing conditions the single band appeared at 190 kd. This represents the β-chain of $\alpha_6\beta_4$, designated herein gp205.

The α-chain, which migrates as a 150 kd band under non-reducing conditions, and a 125 kd band under reducing conditions was detectable only when the cells were metabolically labeled either with [$^{35}$S]-methionine or with tritiated glucosamine. It is believed that the absence of the 125 kd/150 kd bands from the surface-labeled cells is due to an artifact of the iodination procedure.

That gp205 and gp125 components are non-covalently associated with each other at the cell surface was verified by treating FG-met2 cells (a human pancreatic carcinoma line) with a membrane impermeable cross-linker, DTSSP, and lysing the cells with detergent. This resulted in a 400 kd band upon SDS-PAGE. The 400 kd band disappeared and was replaced by 205 kd and 125 kd by subjecting the preparation to reduction, as DTSSP results in reversible cross-linking. The non-covalent complexing of gp205 and gp125 was further confirmed by immunoprecipitating protein from FG-met2 which had been labeled with [$^{35}$S]-methionine. The immunoprecipitate showed an approximate MW of 500 kd as analyzed by gel filtration (The discrepancy in apparent MW is an artifact of the procedures.)

B. PURIFICATION OF gp205 AND gp125

The surface proteins were isolated both from the lung adenocarcinoma cell line UCLA-P3 and from FG-met2.

The cells were grown in sufficient quantity to obtain 50 g wet weight and 20 g wet weight respectively. After washing, the cells were lysed in an equal volume of TBS containing 2% Renex 30, centrifuged at 10,000 x g for 30 min at 4° C. and stored at −70° C.

The lysates were passed sequentially through a Sepharose column and through one or two sequential HB 9318 immunosorbent columns at 5-10 ml/hr. After washing with TBS containing 0.1% Renex 30, pH 8. 5 to remove unabsorbed material, the HB 9318 column was inverted, washed with 3 column volumes of TBS, pH 8.5 containing 1.0% n-octyl β-D-glucopyranoside, and the bound material eluted with 50 mM diethylamine, pH 11.5 containing 150 mM NaCl, 1.0% n-octyl β-D-glucopyranoside. Eluted material was collected in 1.5 ml Eppendorf tubes containing 0.1M Tris HCl pH 6.8, 150 mM NaCl, and 1.0% n-octyl β-D-gluco pyranoside, to lower the pH rapidly to approximately 8.5. Elution was detected by SDS-PAGE stained with silver stain or Coomassie blue, and eluate from peaks containing protein was pooled and concentrated.

C. AMINO ACID SEQUENCING OF PURIFIED ANTIGEN

Figure 4:
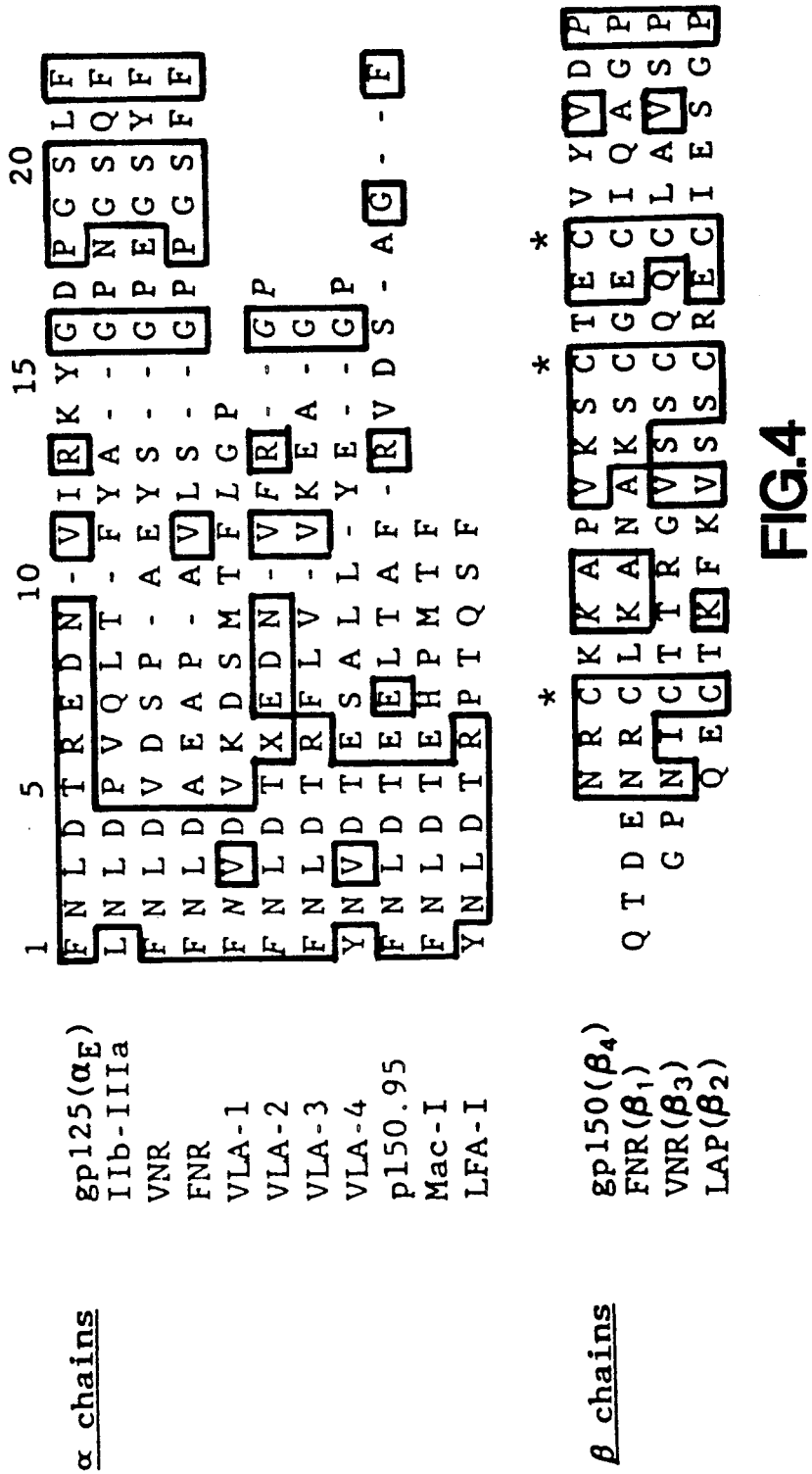
FIG. 4 shows a comparison of N-terminal sequences of various integrin $\alpha$- and $\beta$-chains.

Antigen corresponding to gp205 and to gp125, purified as above was subjected to amino acid sequencing from the N-termini using standard techniques. The gp125 fragment had the N-terminal sequence: F-N-L-D-T-R-E-D-N-V-I-R-K-Y-G-D-P-G-S-L-F which shows extensive homology with a N-terminal sequences of α-chains in other integrins, as illustrated in FIG. 4. (FIG. 4 is a comparison of N-terminal sequences of alpha Chains from gp205,125 and Other Integrins. Amino acids are in the one-letter code. Dashes indicate residue identity with the top sequence, and blanks absence of sequencing information. Abbreviations and sources are: FNR=fibronectin receptor (Argraves et al, *J. Cell Biol.* (1987) 105:338-340; VLA-1 through -4 (Takada et al., *Proc. Nat'l Acad. Sci. USA* (1987) 84:3239-3243)-; Mac-1 (Springer et al., *Nature* (1985) 314:540-542); p150,95 (Miller et al., *J. Immunol* (1987) 138:2381-2383); LFA-1 (Springer et al., *Nature* (1985) 314:540-542); platelet IIb-IIIa (Poncz et al., *J. Biol Chem.* (1987) 262:8476-8482); VNR=vitronectin receptor (Suzuki et al., *Proc. Nat'l Acad. Sci. USA* (1986) 83:8614-8618); PS=fruitfly position-specific antigens (Leptin et al, *EMBO J* (1987) 6:1037-1043). Except for PS, all sequences are of human origin.)

The gp150 fragment had the N-terminal sequence: N-R-C-K-K-A-P-V-K-S-C-T-E-C-V-Y-V-D-P which shows extensive homology with β N-terminal P47 sequences of β-chains in other integrins, as illustrated in FIG. 4.

Figure 3B:
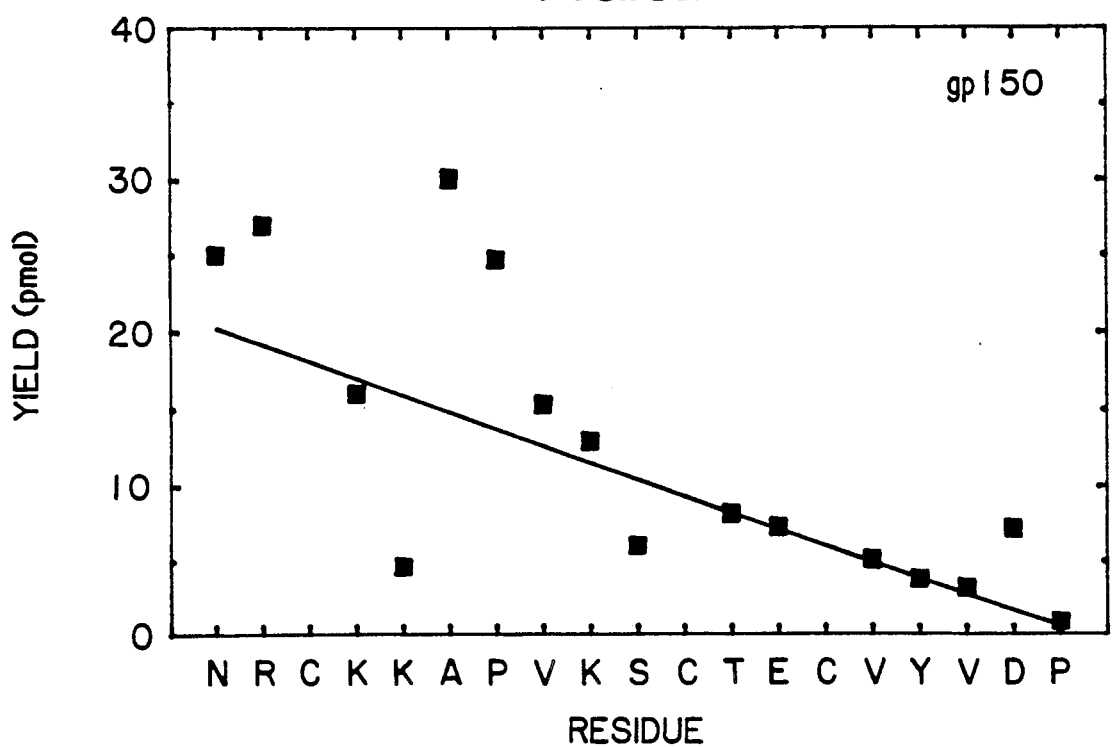

In addition, FIGS. 3A and 3B show the amino acid residue sequences of the gp125 α-chain and the gp150 as precipitated by the HB 9318 antibody.

The gp205 β-chain is apparently blocked at the N-terminus.

Automated microsequencing of gp125, purified on an HB 9318 immunoaffinity column from either carcinoma cells or placental tissues yielded information up to residue 21. The sequences of gp125 from these two sources were identical, with the exception of position 6 which could not be assigned for carcinoma gp125 in three separate sequencing runs. The gp125 sequence showed several similarities with integrin α chain N-termini, as depicted in FIG. 4. The first five residues, FNLDT, are identical in four α-chains, and occur with one replacement in four other α-chains and with two replacements in the remaining three α-chains. Another segment of significant homology among α-chains occurs between residues 15 and 21. In this region, gp125 shares one residue with at least one other α-chain at five positions, and at three positions has unique residues. Overall, the homology of gp125 to the integrin α-chains appears to be equivalent to the homology of the α-chains to each other. The highest level of similarity was observed with the VLA-2 α-chain, where eleven of thirteen residues available for comparison are shared.

Placenta gp150 was sequenced up to residue 19 (FIG. 3B). When this sequence was compared to the amino termini of the three human integrin β-chains, several similarities were found (FIG. 4). Of particular importance is the exact correspondence of the three cysteines, the serine in position 10 and the proline in position 19, as these residues are invariant among integrin β-chains. Overall, gp150 showed eleven identities with β$_1$, eight with β$_2$ and seven with β$_3$. However, the gp150 sequence was distinct from those of the other β-chains since its N-terminus was offset with respect to B (as predicted from cDNAs) and β3 sequences, and since it contained six unique residues (FIG. 4).

To further check the relationship between gp150 and gp180, placental gp180 was also sequenced up to residue 13. This sequence was identical to gp150 (not shown), except for four residues of uncertain assignment, thus providing further evidence for the structural similarity of gp150 and gp180. However, gp205 is undetectable in placental lysates, and two attempts to sequence carcinoma-derived gp205 failed, presumably due to insufficient quantities and/or N-blocking during purification.

D. TWO-DIMENSIONAL GEL ANALYSES

Immunoprecipitations were carried out by overnight incubation of cell lysates with immunoabsorbants prepared by activated-CNBr conjugation of Mab to Sepharose 4B-CL beads (Pharmacia, Uppsala, Sweden). After elution in 8M urea at room temperature, samples were analyzed by two-dimensional electrophoresis, consisting of nonequilibrium pH electrophoresis on tube gels in the first dimension, followed by SDS-PAGE on 7.5% acrylamide slab gels. Gels were impregnated with 2, 5,-diphenyloxazole, dried and exposed for the indicated times to Kodak XAR-5 X-ray film at −70° C. The resulting pattern of migration is shown in FIG. 1.

E. BINDING TO LECTINS

When radiolabeled lysates were preabsorbed with lentil lectin-agarose beads (Vector Labs, Burlingame, Calif.), the antigens reactive with HB 9318 were removed. Removal of antigen was shown by immunoprecipitation of bead supernatant, followed by SDS-PAGE. Similar treatment of radiolabeled lysates with wheat germ agglutinin-agarose beads (E.Y. Labs., San Mateo, Calif.) did not remove the HB 9318 antigen. Therefore, the antigen reactive with HB 9318 was characteristically bound to lentil lectin, but not to wheat germ agglutinin.

F. GEL FILTRATION OF ANTIGEN

Radiolabeled detergent cell lysates were absorbed on wheat germ agglutinin-Sepharose columns (E.Y. Labs, San Mateo, Calif.), The breakthrough was absorbed onto lentil lectin-Sepharose columns. After washing, the absorbed material was eluted by the addition of 2% alpha methyl-mannoside (Sigma Chemical Co., St. Louis). The eluted material was subjected to gel filtration, in the presence of 10 mM Tris, pH 8.0 containing 0.15M NaCl, 1 mM $CaCl_2$, 1 mM $MgCl_2.6H_2O$, 0.02% sodium azide and 0.1% Renex 30 by using an FPLC instrument (Pharmacia, Uppsala, Sweden), equipped with a Sepharose 6 column. Molecular weight standards were run in parallel. One ml fractions were collected (approximately 40 fractions), and subjected to immunoprecipitation with HB 9318 antibody. SDS-PAGE analysis of immunoprecipitates revealed that the following molecular species were reactive with HB 9318 in the indicated fractions:

| SDS-PAGE m.w. | Fraction # | FPLC MW |
|---|---|---|
| 135; 205 | 25 | 669 kd |
| 135; 205 | 26 | 669 kd |
| 135; 150; 205 | 27 | approximately 669 kd |
| 135; 150; 205 | 28 | approximately 669 kd |
| 135; 150; 205 | 29 | between 669 kd and 440 kd |
| 135; 150 | 30 | between 669 kd and 440 kd |
| 135; only | 31–36 | between 440 kd and 232 kd |

The estimated molecular weights corresponding to the FPLC fractions are indicated in the right column. Since the estimated MW exceeds the MW determined by SDS-PAGE, the HB 9318 antigens must exist as multimeric complexes, probably heterodimers formed by the association of one 205 kd component with one 125 kd component. The presence of excess free 125 kd component was also suggested by the material immunoprecipitated from fractions 31–36.

G. PULSE CHASE BIOSYNTHETIC STUDIES:

Single cell suspensions of exponentially growing FG cells were propagated for one hour at 37° C. in methionine-free medium (Irvine Scientific, Santa Ana, Calif.) and then pulse labeled for 10 min with [$^{35}$S]-methionine (1295 Ci/mM NEN Research Products, Boston, Mass.) at a concentration of 1.0–1.5 mCi/$3 \times 10^7$ cells/ml. After the removal of an aliquot of $5 \times 10^6$ cells that constituted the zero-time point, the remaining cells were washed three times with cold Tris buffer, pH 7.5 containing 10 mM unlabeled L-methionine (Sigma Chemical Co., St. Louis Mo.). The labeled cells were resuspended in complete medium containing 10 mM unlabeled methionine and incubated on a shaker at 37° C. Aliquots were removed at the different time points indicated and the cells were centrifuged and extracted in RIPA lysis buffer as previously described.

After a 10 minute pulse with [$^{35}$S]-methionine, a faint band of 150 kd was detected at the zero time point of chase. This 150 kd component was clearly visible after 15 minutes of chase. Within the next 45 minutes of chase it appeared to be processed and the appearance of the 135 kd component Was seen. Both the 205 kd and 135 kd molecules were detectable after 4 hours of chase until up to 20 hours of chase. It is presently not clear whether a precursor/product relationship exists between the two forms of the HB 9318 antigen. While not wishing to be bound by the explanation, it appears that post translational processing of the 150 kd molecule gives rise to the 135 kd subunit. Moreover, the 205 kd component could either arise by further processing of 135 kd component or by altered processing of the 150 kd precursor. Alternatively, it could have its own precursor molecule that is not recognized by Mab HB 9318, thereby suggesting that the HB 9318 antigen is a heterodimer comprised of two distinct non-covalently linked subunits.

Western blots of material immunopurified with HB 9318 from carcinoma cells and placental tissue in which 5710 antiserum reacted predominantly with gp205, gp180, and gp150 and displayed little, if any, reactivity with gp125. This antigenic similarity of gp205, gp80, and gp150 was authentic since, in a further refinement, antibodies that were adsorbed and eluted from gp150 reacted with gp180 (in addition to gp150 itself). Antibodies adsorbed and eluted from gp180 reacted with gp150 (in addition to gp180 itself).

Furthermore, $^{35}$S-methionine labeled gp205, gp180, gp150 and gp125 purified by immunoaffinity and electroelution were subject to "hot" blotting with gp150 purified antibodies. These antibodies only reacted with gp205, gp180, and gp150, but not with gp125. Subsequent autoradiography of the blot confirmed that the four proteins were present in approximately equal amounts. These results provided further evidence for the structural relatedness for gp205, gp180, and gp150, and for the dissimilarity of gp125. Therefore, co precipitation of gp125 by HB 9318 and 5710 antibodies is probably due to noncovalent associations with gp205, gp180 and gp150.

H. LIMITED PEPTIDE MAPPING

Limited peptide mapping was used to determine the structural relationships between gp205 and gp125. Cells labeled with [$^{35}$S]-methionine were immunoprecipitated with HB 9318 and subjected to SDS-PAGE. The bands to be analyzed were located on the dried gel by autoradiography. These bands were then excised from the gel, rehydrated and inserted in slots on a 15% acrylamide SDS-PAGE gel containing a 0.5 microgram/ml solution of *Staphylococcus aureus* V8 protease (Cleveland, et al. (1977) *J. Biol. Chem.* 252: 1102–1106.) After the bands were stacked, electrophoresis was suspended for 30 min. to allow enzymatic digestion. The gels were thereafter fluorographed.

SDS-PAGE resolved eight peptides for gp205 and ten peptides for gp125. Each generated distinct profiles, suggesting that gp205 and gp125 are structurally unrelated. HB 9318 precipitates two minor bands, gp180 and gp150. Limited peptide mapping of gp180 resolved seven fragments; gp150 resolved six fragments. The fragments of both gp180 and gp150 co-migrated with gp205 fragments, except for one gp150 peptide which co migrated with the major fragment of gp125. (Due to its significantly greater intensity, this fragment may be derived from minor contamination of gp150 with the closely-spaced gp125.) These data suggest that gp205, gp180, and gp150 are structurally related, but distinct from gp125.

This conclusion was further supported by investigations with a polyclonal antiserum (5710) raised against antigen purified from carcinoma cells by immunoaffinity chromatography on the monoclonal antibody HB 9318. Antiserum 5710 was prepared by bleeding of an NZW rabbit, subcutaneously injected with approximately 2 micrograms of immunopurified carcinoma HB 9318 antigen at day 0 in Freund's complete adjuvant, and at days 30 and 45 with the same amount of antigen in incomplete adjuvant.

From carcinoma lysates, the 5710 antiserum precipitated a set of proteins identical to those reactive with HB 9318. If, however, the cell lysates were previously treated at 100° C. in the presence of SDS to disrupt noncovalent associations, then antiserum 5710 precipitated only gp205, gp180 and gp150, but not gp125. The isolated gp205, gp180 and gp150 displayed their characteristic $M_r$ downshift under nonreducing conditions. These results suggest that at least some of the epitopes present on gp205, gp180 and gp150 are not found on gp125 and that all 5710 epitopes on gp125, if any, are sensitive to denaturation. This conclusion was verified by Western and "hot" blots.

I. WESTERN AND "HOT" BLOTS

The general procedure of Towbin, H. et al. (1979) *Proc. Nat'l Acad. Sci. USA* 76:4350–4354, was followed. Proteins separated by SDS-PAGE on a 5% gel were transferred overnight at 4° C. to Immobilon (Millipore Corp., Bedford Mass.) using a 25 mM Tris, 192 mM glycine buffer. The filter was saturated with 3% (w/v) nonfat dry milk in TBS, pH 8.0 with 0.05% Tween 20 and 0.02% azide, incubated for 3 h with primary antibody, washed, overlaid for 1 hour with alkaline phosphatase-conjugated goat anti-rabbit (Promega Biotec, Madison, Wis.) or anti mouse (Boehringer Mannheim, Indianapolis, Ind.) IgG, washed again and then developed with 0.33 mg/ml 5-bromo-4 chloro-3-indolyl phosphate in 100 mM Tris-HCL pH 9.5, 100 mM NaCl, 5 mM MgCl$_2$, followed by 5 mM EDTA in 20 mM Tris HCl pH 8.0. For affinity purification (Weinberger, C., et al. (1985) *Science* 228:740–742) of 5710 antibodies, vertical strips cut from the edges of gp205, gp125 whole gel blots previously incubated with 5710 were developed to locate reactive bands. Horizontal strips corresponding to these were excised from the undeveloped mid-part of the filter. Bound antibodies were eluted by three one-minute washes with 5 mM glycine-HCl pH 2.3 containing 150 mM NaCl, 0.05% Tween 20, 100 micrograms/ml bovine serum albumin, 2.5 mM sodium azide, and quickly neutralized by addition of Tris-HCl pH 8.0.

For "hot" blots, 1×10$^7$ cells were metabolically labeled with [$^{35}$S]-methionine, immunoprecipitated with HB 9318 and electrophoresed on a 5% SDS-PAGE gel. The wet gel was autoradiographed overnight to locate radioactive bands, which were then excised. Proteins were electroeluted in an ISCO apparatus as described (Hunkapiller M. W., et al (1983) *Methods Enzymol.* 1:399–413), run on a 5% SDS-PAGE and transferred to Immobilon filters. The filters were first immunostained and then autoradiographed.

EXAMPLE 5
ADDITIONAL BIOCHEMICAL CHARACTERISTICS OF HB 9319 ANTIGEN
A. MOLECULAR PROFILE UNDER NON-REDUCING CONDITIONS

FG-met2 cells labeled with [$^{35}$S]-methionine were immunoprecipitated using HB 9319 and analyzed by SDS PAGE under non-reducing conditions. HB 9319 antigen migrates as a single band of 125 kd under these conditions.

B. EXTRINSIC RADIOLABELING WITH $^{125}$I

Cultures of FG-met2 cells were surface iodinated using $^{125}$-I sodium iodide, and detergent lysates were immunoprecipitated with HB 9319. The precipitated antigen migrates on SDS-PAGE under reducing conditions as a single species of 140 kd.

Similar results were obtained when the antigen was labeled metabolically with labeled inorganic sulfate or phosphate.

C. TWO-DIMENSIONAL GEL ANALYSIS

The method follows that of Example 4(E) using HB 9319 in place of HB 9318. The resulting pattern of migration is shown in FIG. 2.

D. TREATMENT WITH GLYCOLYTIC ENZYMES

The antigen recognized by HB 9319 is isolated by immunoprecipitation of radiolabeled cell lysates. The immunoprecipitates are treated with a variety of exoglycolytic and endoglycolytic enzymes. After treatment the apparent mobility of the precipitated antigens is determined in a SDS-PAGE system. The glycolytic enzymes characteristically modify the apparent molecular weight of the HB 9319 antigens, by removing discrete portions of O-linked or N-linked glycans. The results obtained can be schematically summarized as follows:

| Enzyme | Apparent MW After Treatment |
| --- | --- |
| Endo H | 140 kd |
| NA | 135 kd |
| Endo N | 140 kd |

E. BINDING TO LECTINS

The method follows that of Example 4(E), using HB 9319 in place of HB 9318. When radiolabeled lysates were preabsorbed with lentil lectin-agarose beads, the antigens reactive with HB 9319 were removed. When they were preabsorbed with wheat germ agglutinin agarose beads, the antigens were not removed. Removal of antigen was shown by immunoprecipitation of bead supernatant, followed by SDS-PAGE. Therefore, the antigen reactive with HB 9319 characteristically binds to lentil lectin, but not to wheat germ agglutinin.

F. BIOSYNTHESIS OF HB 9319 ANTIGEN

The method is as described in Example 4(G). Pulse-chase biosynthetic studies revealed the presence of a precursor molecule of 120 kD after a 10 minute pulse with [$^{35}$S]-methionine. At the 15 minute time point of chase small amounts of the 140 kda HB 9319 antigen were also visible. Both of these molecules were observed to be present until 60 minutes after chase. However, only the 140 kd molecule was detectable at 4 hours after chase until 20 hours after chase. Thus, the 120 kd component serves as a precursor for the 140 kd component of the HB 9319 antigen.

EXAMPLES OF USES FOR THE PRESENT INVENTION

V. CLONING AND SEQUENCING OF $\alpha_6\beta_4$

A. CELLS, LABELING AND ANTIBODIES

The human pancreatic carcinoma cell line FG was cultured as described previously (Kajiji et al. (1989) *EMBO J.* 8:673-680). The human colon carcinoma cell line LoVo (Drewinko et al. (1976) *Cancer Res.* 36:467-475) was obtained from ATCC and cultured in Dulbecco's modified MEM (DMEM). Both RPMI 1640 and DMEM were supplemented with 10% fetal calf serum, 2 mM glutamine and penicillin streptomycin (50 IU/ml-50 µg/ml). Human platelets were the generous gift of Dr. Mark Ginsberg (Research Institute of Scripps Clinic.)

Cell Labeling

FG cells ($10^7$) were metabolically labeled with [$^{35}$S]-methionine as described previously (Kajiji et al., (1989), supra. Platelets were with [$^{125}$I] sodium iodide and lactoperoxidase essentially as described by Roth (1975) *Methods Enzymol.* 37(Pt. B):223-233. Preparation of nonionic detergent cell extracts, immunoprecipitation, and analysis by SDS-PAGE have been described previously (Kajiji et al., (1989), supra).

Antibodies

The mouse monoclonal antibody S3-41 (HB9318) and the rabbit polyclonal antibody 5710 recognize $\alpha_6\beta_4$ (Kajiji et al. (1987) *Cancer Res.* 47:1367-1376; (1989), supra. The rat monoclonal antibody GoH3 (Sonnenberg et al, (1987), supra, which is specific for $\alpha 6$ was the generous gift of Dr. Arnold Sonnenberg. The "anti-$\alpha 6$ cyto" rabbit antiserum was raised to a synthetic peptide (IHAQPSDKERLTSDA) corresponding to the carboxy-terminus of $\alpha 6$ based on the deduced amino acid sequence of the $\alpha 6$ cDNA clones isolated in this study. (FIG. 9) (In FIGS. 9A-9E, potential sites of N-linked glycosylation are shown in bold face; the sequence corresponding to the amino terminus sequence determined on B4 protein (Kajiji et al., (1989), supra, is underlined with a lightly shaded bar; the putative transmembrane region is underlined with a dark bar; possible alternative splice regions are boxed; the position of another 159 bp insert is denoted by an arrowhead; the sequence data are available from EMBL/GenBank/DDBJ, Accession No. X53587.) The monoclonal antibody, AA3, was produced using standard hybridoma procedures (Kohler and Milstein (1975), supra) from mice immunized with placental $\alpha_6\beta_4$ purified on affinity column coupled with the monoclonal antibody S3-41 as described by Kajiji et al. (1989), supra. AA3 has been shown to be specific for the $\beta 4$ subunit.

B. CDNA LIBRARY SCREENING. CDNA SYNTHESIS AND POLYMERASE CHAIN REACTION (PCR)

Three different cDNA libraries were constructed (Invitrogen, San Diego, Calif.) from mRNA isolated from FG cells: an oligo-dt primed expression library in λgt11 and two plasmid (pTZ18R Bst XI, Invitrogen) libraries, one oligo-dT primed and the other random-primed.

The following oligonucleotides were synthesized with a Gene Assembler (Pharmacia, Uppsala, Sweden) according to the amino terminus sequence of the mature $\alpha 6$ protein 1) 40-mers with 64-fold redundancy covering the first 13 amino acids (FNLDTREDNVIRK)

```
5'-TTCAACTTAGACACGCGAGAGGACAACGTAATCCGAAAGT-3'.
      C             C       C  C         C
```

2) 14-mers covering the complete redundancy of The first 5 amino acids
1)
```
5'-TTAATCTAGATAC-3'
    C  C  C  C
```

2)
```
5'-TTTAATCTGGATAC-3'
     C  C  C   C
```

3)
```
5'-TTTAATTTGGACAC-3'
     C  C   C  C
```

Screening of the random-primed cDNA library was performed with the 40-mers, labeled with [$\gamma^{32}$]p ATP and T4 polynuoleotide kinase (labeling kit, Pharmacia), using low stringency conditions (hybridization at 37° C. overnight and washes with 2X SSC at room temperature and at 46° C., 30 min each). Forty-four positives were then hybridized with the complete set of 14-mers followed by washes in 3.0M tetramethylammonium chloride (TMAC) at progressively higher temperatures as described by Wood et al. (1985) *Proc. Nat'l Acad. Sci.* 82:1585-1588. Three clones, $\alpha 6.1$, $\alpha 6.31$, and $\alpha 6.44$ remained positive up to the melting temperatures of 14-mers (46° C.).

The insert from the $\alpha 6.1$ cDNA clone was isolated and used to screen the oligo-dT primed cDNA library. Preparation of probes, filters, hybridization, and washes were performed according to Maniatis et al. (1982) Molecular Cloning: A Laboratory Manual (Cold Spring Harbor, N.Y.).

The λgt11 library was screened (Young and Davis, (1983) *Proc. Nat'l Acad. Sci.* 80:1194-1198), with the rabbit antiserum 5710, which was raised against purified human $\alpha_6\beta_4$ and previously shown by Western blots to react predominantly with $\beta_4$ (Kajiji et al., (1989) supra. Positive clones from the antibody screening were plaque purified and the cDNA inserts were amplified directly from bacteriophage plaques using the polymerase chain reaction (PCR). Briefly, a plug of agar containing the plaque was transferred to 1 ml of SM (10 mM Tris-HCl pH 8.0, 50 mM NaCl, 5 mM MgCl$_2$) and incubated for either 1 h at room temperature or overnight at 4° C. 10 μl of supernatant was used in a 50 μl PCR containing 67 mM Tris-HCl pH 8.8, 1.5 mM MgCl$_2$, 10 mM B-mercaptoethanol, 1.25 units of TAQ I Polymerase, 0.25 mM each of dATP, dTTP, dCTP, and dGTP, and 0.1 μg each of 24-mer oligonucleotides corresponding to sequences of λgtII flanking the EcoRI cloning site. The PCR program consisted of 3 steps: 1) one cycle at 94° C. for 4 min; 2) 40 cycles of 1 min at 94° C., 2 min at 55° C., and 3 min at 72° C. with a 5 second per cycle extension on the 72° C. segment; 3) 10 min at 72° C. and a final shift to 4° C. These amplified fragments were isolated using Gene Clean (Bio 101, La Jolla, Calif.), digested with either EcoRI or NotI, repurified with Gene Clean and subcloned into pKS+ (Stratagene, La Jolla, Calif.).

Fusion proteins produced by the positive clones were used to select epitope-specific antibodies (Weinberger et al., (1985), supra) from the rabbit antiserum, 5710. These antibodies were tested for their ability to immunoprecipitate $\beta_4$ from a denatured FG lysate. The clone, Iam 18.2.1, was identified as a $\beta_4$ clone by this epitope selection method. The insert from this clone was used to screen both of the plasmid cDNA libraries to isolate overlapping clones. Additional screenings were done using radiolabeled inserts from $\beta_4$ positive cDNA clones until the complete $\beta_4$ cDNA was isolated.

cDNA Synthesis and Polymerase Chain Reaction (PCR)

Poly-A+ RNA was isolated from human placenta and human carcinoma cells (Fast Track Kit, Invitrogen Corp.) and 2-5 μg were used to synthesize cDNAs with AMV Reverse Transcriptase (20 units, Molecular Genetics Resources, Tampa, Fla.) and 1 μg of random hexamer primers (Pharmacia). The cDNAs were extracted with phenol/chloroform, precipitated with ethanol and resuspended in 100 μl of water. One μl was amplified using the PCR conditions described above except for the primer concentrations (1 μM each) and, for reactions using oligos 3+4 and oligos 5+6, the annealing temperature (52° C.). The following oligonucleotides were used (see FIGS. 9A-9E for numbering; 5' nucleotide is in boldface type: 1) (82-98), 2) (310-329), 3) (4441-4482), 4) (4679-4697), 5) (4679-4697), and 6) (4805-4820). Ten μl of the PCR mixture were separated on a 3.5% acrylamide gel (TBE) along with 1 kb molecular size markers (BRL, Gaithersburg, Md.) and the DNA was visualized by staining with ethidium bromide.

Based on the sequence of the amino terminus for $\alpha_6$ (FIGS. 6A-6D) degenerate oligonucleotides were synthesized and used to screen 3×10$^5$ colonies from a random primed human pancreatic carcinoma (FG) cDNA library as described supra. (In FIGS. 6A-6D, the sequence corresponding with the amino-terminal sequence determined on α6 protein (Kajiji et al., (1989), supra) is underlined. The putative transmembrane region is shown by a dashed underline. The arrowhead marks the position of cleavage between the signal sequence and the mature protein. Cysteines are circled. Potential sites of N-linked glycosylation are shown in bold face. Closed boxes outline the putative cation binding domains. Dashed boxes outline dibasic residues that may represent sites of cleavage in the formation of a heavy and a light chain. The cytoplasmic sequence GFFKR, which is conserved in virtually all of the integrins α chains, is denoted by a stippled dashed box. A potential polyadenylation signal is boxed. These sequence data are available from EMBL/GenBank/DDBJ under accession number X53586).

Three clones with inserts of about 1.2 kb were isolated and sequenced. All three clones (α6.1, α6.31, and α6.44) overlapped and contained open reading frames (ORFs) whose deduced amino acid sequence matched exactly the protein sequence of the amino terminus of α6 (Kajiji et al., (1989) supra: Hemler et al., (1989), supra.

Figure 5A:
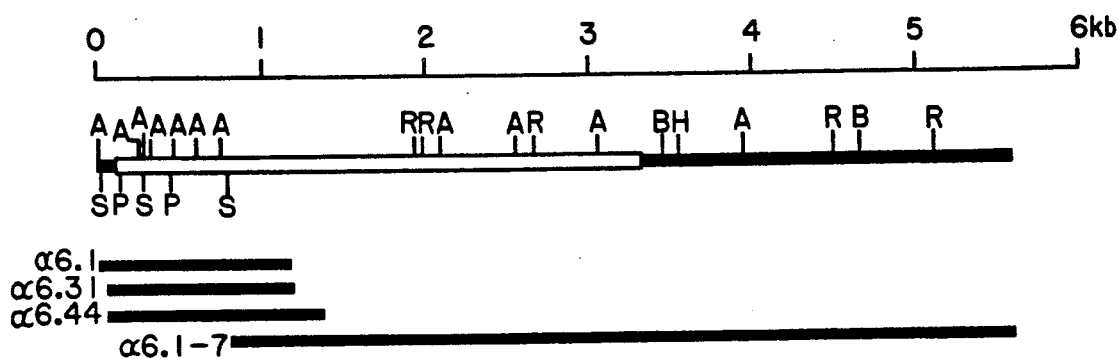
FIGS. 5A and 5B are diagrams showing the restriction maps of the $\alpha_6$ and $\beta_4$ cDNA clones; $\alpha_6$ is shown on the top under FIG. 5A, $\beta_4$ is shown layer under FIG. 5B.

To isolate the rest of the $\alpha_6$ gene, approximately 7.2×10$^5$ colonies of the oligo-dT Primed cDNA plasmid library was screened with the radiolabeled insert from the α6.1 clone. Of 16 positive clones, one (α6.1-7) had an insert of 4.8 kb. Overlapping restriction endonuclease fragments of the α6 cDNA inserts were subcloned into pKS and sequenced in both orientations. FIG. 5A shows the overall relationship of the $\alpha_6$ cDNA clones to one another and the restriction sites relevant for subcloning and sequencing. (In FIGS. 5A and 5B, the ORFs for $\alpha_6$ and $\beta_4$ are shown as open bars; the lines indicate the size and position of the plasmid and phage cDNA clones isolated from the three cDNA libraries; restriction sites relevant to subcloning and sequencing are AvaI (A), Bam HI (B), PvuII (P), EcoRI (R), and Sma I (S); representative clones out of a total of 54 are shown for $\beta_4$). The resulting sequence consists of 146 bp of the 5'-untranslated region, an ORF of 3219 bp encoding 1073 amino acids, and 2264 bp of the 3'-untranslated region (FIGS. 6A-6D).

2. ISOLATION OF cDNA CLONES ENCODING B$_4$

Seventy-two of approximately 1×10$^6$ plaques of a λgtII FG expression library were positive with an anti-$\beta_4$ rabbit antiserum (5710, Kajiji et al., (1989), supra. These positives were arranged into 11 groups based on cross-hybridization of the inserts, which were amplified by PCR. A representative insert from each group was subcloned and sequenced. None of these inserts, however, contained ORFs with obvious homology to integrin β-chains. Subsequently, these phage clones were tested by "epitope selection" (Weinberger et al., (1985), supra) with the 5710 antiserum. After induction with IPTG, fusion proteins bound to Nylon filters were used to adsorb and elute specific antibodies from the 5710 antiserum. These antibodies were tested by immunoprecipitation of a SDS/heat denatured radiolabeled FG cell detergent lysate. One of the clones, lam-18.2.1, which was part of a group containing 13 cross-hybridizing positives, yielded antibodies reactive with a protein with SDS-PAGE mobility identical to the 205 kD form of $\beta_4$ (FIG. 7A; Antibodies eluted from plaques lam 23.1.1 (lane 1), lam 8B (lane 2), and lam 18.2.1 (lane 3) were used for immunoprecipitations of a denatured [$^{32}$S]methionine FG lysate and analyzed by SDS-PAGE under reducing (R) or nonreducing (N) conditions). The sequence of lam-18.2.1 contains an ORF encoding 612 amino acids, not homologous to the other integrin β-chains, followed by a noncoding region and a poly(A) tract. Since $\beta_4$ is much larger than the other β-chains (205,000 vs. 95,000-130,000) the lam 18.2.1 sequence could represent an extension of the carboxy-terminus. Plasmid libraries made from FG cell mRNA were screened with the lam-18.2.1 insert, in order to isolate inserts extending in the 5' direction.

Figure 5B:
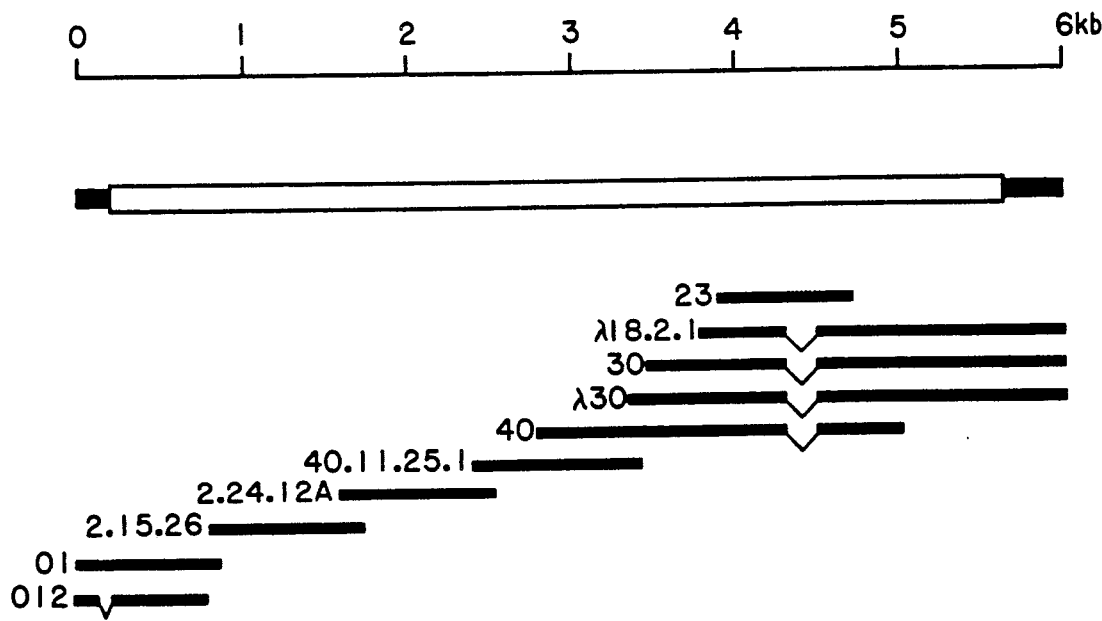

By this procedure a series of overlapping clones covering approximately 5.5. kb were progressively isolated and sequenced (FIG. 5B; see discussion of FIG. 5A for description; representative clones out of a total of 54 are shown for β4). An ORF encoding 1822 amino acids was located (FIGS. 8A and 8B), initiating with a stretch of 27 relatively hydrophobic residues, probably representing a signal peptide, followed by the sequence NRCKKAPVCDECV (determined by amino acid sequencing). (In FIG. 8A, the beginning and end of the sequence as well as the position of the predicted transmembrane segment (dark bar underline) are shown for orientation; the region containing the amino-terminal sequence determined on β4 protein (Kajiji et al., 1989), supra. is underlined with a lightly shaded bar; alternate splice regions are boxed; the arrowhead at base pair 4,744 shows the site of insertion of the 159-bp stretch reported by Hogervorst et al. (1990) supra: the complete sequence data (5,918 bp) are available from EMBL/GenBank/DDBJ under accession number X53587.) Within the first 710 amino acids of this deduced sequence, homology to the other integrin β-chains was obvious, including conservation of cysteines at 47 of 56 positions. After this region of homology, there is a hydrophobic stretch of 23 amino acids, probably representing a transmembrane segment, followed by 1,089 amino acids which presumably represent an unusually large cytoplasmic domain. The total mass of the mature protein encoded by this ORF is 200,000. The addition of carbohydrates at the 5 extracytoplasmic putative N-glycosylation sites would result in a protein of $M_r$ 212,500 which is consistent with the $M_r$ of β4 on SDS polyacrylamide gels. These results identify the cDNAs that we have isolated from carcinoma cells as corresponding to the β4 subunit.

To test whether or not the large carboxy terminal sequence was part of the β4 protein in complex with α6, a native FG lysate was immunoprecipitated with the antibodies eluted from the cytoplasmic domain fusion protein (clone lam-18.2.1). These antibodies precipitated a complex of proteins with SDS-PAGE mobilities identical to those of authentic α6β4 heterodimers (FIG. 7B; β4 specific monoclonal antibody, AA3 (lane 1), and antibodies eluted from plaque lam 18.2.1 (lane 2) were used for immunoprecipitations of a nondenatured [$^{35}$S] methionine FG lysate and analyzed by SDS-PAGE under reducing (R) or nonreducing (N) conditions.)

From the isolated cDNA clones encoding both α and β subunits of the epithelial integrin α6β4, the α subunit was sequenced from two overlapping clones encoding a protein of 1073 amino acids. Identification of these clones as α6 came from two pieces of evidence. First, the ORF contained a sequence which matched exactly the sequence of the amino terminus of the mature α6 protein (Kajiji et al., (1989), supra). Second, an antiserum to a synthetic peptide corresponding to the putative carboxy-terminus in the ORF recognized the α6β4 complex in immunoprecipitations of radiolabeled carcinoma cell lysates.

C. DNA SEQUENCING

The α6 cDNA clones were sequenced from restriction fragments (PvuII or SmaI for α6.1; AvaI + BamHI or EcoRI + HindIII for α6.1-7) subcloned into pKS+. The β4 cDNA clones were sequenced from nested deletion subclones created using a kit from Pharmacia. Both strands were sequenced by the (Sanger) dideoxy chain termination technique using either an ABI 370A DNA Sequencer from Applied Biosystems (Foster City, Calif.) or the Sequenase kit from United States Biochemical Corporation (Cleveland, Ohio) utilizing either the T3 and T7 polymerase primer sequences on the vector or specific oligonucleotide primers synthesized to the appropriate regions of the α6 or β4 sequence. Sequences were analyzed on a VAX-VMS version 5.2 computer, with the analysis programs of the University of Wisconsin Genetics Computer Group (Devereux et al., (1984) *Nucleic Acids Res.* 12:387–395).

D. PRIMARY STRUCTURE ANALYSIS OF α6 AND β4

1. Analysis of the Primary Structure of α6

Preceding the amino terminus of the mature protein is a possible signal sequence of 23 amino acids. The mature protein is comprised of 1050 amino acids with a $M_r$ of about 117,000. The addition of carbohydrate with an average 2500 $M_r$ to the protein core at the 10 potential N-glycosylation sites (N-X-S/T) would result in an estimated size of 142,000 $M_r$. This $M_r$ corresponds well with the 150,000 $M_r$ estimated from the migration of α6 on SDS-polyacrylamide gels under nonreducing conditions.

A hydropathy profile (Kyte and Doolittle, (1982) *J. Mol. Biol.* 157:105–132), of the deduced protein sequence identified a putative transmembrane region from amino acid residues 1012–1037. Following this transmembrane region are 36 amino acids (residues 1038 1073) which comprise the presumed cytoplasmic domain. Analysis of the amino terminus portion of the molecule revealed 7 homologous repeats (Domain I, residues 42–79; II=113-145; III=185-217; IV=2-56-292; V=314-352; VI=375-411; VII=430-470). The last three domains each contain a sequence motif resembling the cation binding site consensus sequence of D-X-D/N-X-D/N-G-X-X-D found in a number of calcium-binding proteins (Van Eldik et al., (1982) *Int'l Rev. Cytol.* 77:1–61). A fourth site, residues 230–238, with weak homology to this calcium binding site motif resides between repeated domains III and IV. These potential cation binding sites are in a region (residues 189–488) of the molecule which is devoid of cysteine residues.

The migration of α6 in SDS-polyacrylamide gels under reducing conditions indicated that α6 consisted of two polypeptides joined by a disulfide bridge (Sonnenberg et al., (1987), supra; Kajiji et al., (1989), supra) similar to the integrin α-subunits α5, α$_V$, α$_{IIB}$, and αPS2. In the region of α6 corresponding to this potential cleavage site (residues 899–923), there are three sets of dibasic residues. The use of two of these sites could account for the appearance of the smaller polypeptide as a doublet on SDS-polyacrylamide gels (Sonnenberg et al., (1987), supra). This doublet may also arise from differences in glycosylation at the two sites present in the light chain. The sequence RKKRE, which most closely resembles the cleavage site of other integrin α-chains is at position 899–903. Cleavage at this site would result in the formation of a heavy chain of 118,000 $M_r$ and a light chain of 24,000 $M_r$ which are close to the 125,000 $M_r$ and 30,000 $M_r$ observed by SDS-PAGE.

A COMPARISON OF α6 WITH THE OTHER INTEGRIN α-SUBUNITS

Alignment with the other integrin α-subunits showed that α6 shares several structural features with these proteins. Of the 20 cysteines in the mature $\alpha_6$ protein, 11 are in equivalent positions to those found in the other 10 $\alpha$-chains, 5 are shared with 9 of the other 10 $\alpha$s, and 2 are shared with the other 5 $\alpha$-chains which do not contain the I domain. One cysteine (residue 1039) is shared with the PS2 $\alpha$-chain, and another cysteine (residue 643) is unique to $\alpha_6$. Cysteine 643 is in a region of the molecule (residues 641–689) in which two gaps of about 15 and 9 amino acids were placed in the other o-chains in order to optimize the alignment. Three of the four putative cation binding sites of $\alpha_6$ align with similar sites in the other $\alpha$-subunits. A fourth weakly homologous cation binding site (residues 230–238) precedes, other $\alpha$-chains which lack the I domain. The cytoplasmic domain of $\alpha_6$ contains the sequence GFFKR which is absolutely conserved in all but the Drosophila PS2 $\alpha$-subunit, where the K is replaced by an N.

Some of the integrin $\alpha$-chains contain additional polypeptide sequence. $\alpha_2$ and the $\alpha$-chains associated with $\beta_2$ ($\alpha_L$, $\alpha_M$, $\alpha_{P150}$) contain an insert domain (I domain) near the amino terminus of these molecules and the Drosophila PS2 $\alpha$-subunit contains an insert just preceding the transmembrane portion of this molecule. $\alpha_6$ does not contain either of these inserts.

The $\alpha_2$ subunit shares only 18% to 26% identity with the other integrin $\alpha$-subunits. The highest homology $\alpha_V$, $\alpha_5$, and $\alpha_{PS2}$ (25% to 26% identity) and the lowest homology (18% identity) is with those $\alpha$-chains which contain the I domain ($\alpha_M$, $\alpha_L$, $\alpha_{P150}$, and $\alpha_2$).

All of the integrin o proteins contain three potential cation binding sites. A fourth potential site exists in 4 of the $\alpha$-chains which do not contain the I domain. In contrast, $\alpha_6$ lacks this fourth cation binding site which makes it, along with $\alpha_4$, an exception to the classification of the integrin $\alpha$-subunits proposed by Takada and Hemler (1989) *J. Cell Biol.* 109:397–407. There is a site (residues 230–238) with weak homology to the cation binding site consensus sequence. However, this site does not align with a potential site in any of the other $\alpha$-chains, it starts with an asparagine instead of an aspartic acid residue, and it contains a phenylalanine where an aspartic acid or asparagine residue is expected. (These differences are, for the moment, of unclear significance, and await elucidation from X-ray crystallographic data as done for the calcium binding proteins (Strynadka and James, 1989).

B. Further evidence for the identity of the $\alpha_6$ cDNA clones and association of $\alpha_6$ with both $\beta_4$ and $\beta_1$.

Figure 10A:
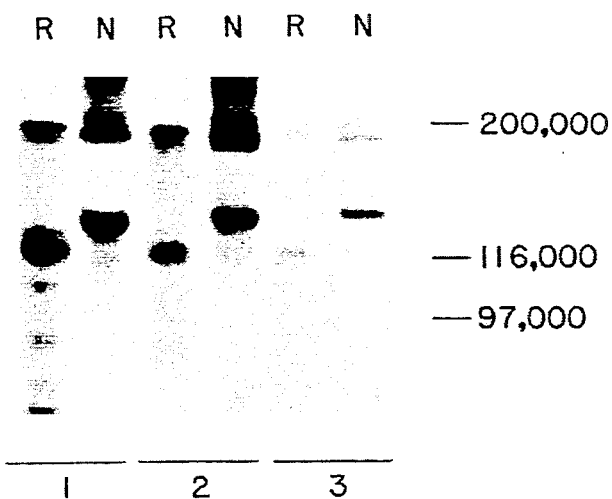
FIGS. 10A and 10B are photocopies of an autoradiogram of $\alpha_6\beta_4$ and $\alpha_6\beta_1$ immunoprecipitated with anti-$\alpha_6$ cyto, a polyclonal antibody raised to a synthetic peptide corresponding to the carboxy terminus of $\alpha_6$.
Figure 10B:
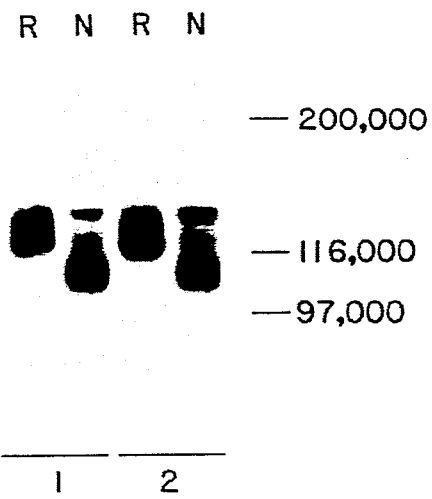

A rabbit antiserum (anti-$\alpha_6$ cyto) was prepared to a synthetic peptide corresponding to the last 15 amino acids of the deduced $\alpha_6$ amino acid sequence. This antiserum precipitated the $\alpha_6\beta_4$ complex from a radio labeled FG lysate (FIG. 10A; SDS-PAGE under reducing (R) and nonreducing (N) conditions; antibodies used were anti-$\alpha_6$ cyto (lane 1), antiserum 5710 (lane 2), and the monoclonal antibody S3-41 (lane 3), both to $\alpha_6\beta_4$) indicating that the cDNA clones isolated in this study encode the $\alpha_6$ protein. We then tested this antiserum with platelets which express $\alpha_6\beta_1$ (Sonnenberg et al., (1987), supra) but not $\alpha_6\beta_4$. FIG. 10B shows that this antiserum precipitated the $\alpha_6\beta_1$ complex from a radiolabeled platelet lysate. (In this FIG., $^{125}$I surface-labeled platelets were immunoprecipitated with the monoclonal antibody to $\alpha_6$, GoH3 (lane 1) and the antiserum anti-$\alpha_6$ cyto (lane 2).) These results provide further evidence that $\alpha_6$ forms stable heterodimers with both $\beta_1$ and $\beta_4$ (Hemler et al., (1989) supra). However, these results do not exclude the possibility that alternatively spliced forms of $\alpha_6$ may be expressed which could associate preferentially with the different $\beta$-chains.

2. Analysis of the primary structure of $\beta_4$

A series of overlapping cDNA clones was used to deduce and examine the primary structure of the integrin subunit $\beta_4$. Evidence for the authenticity of these cDNAs lies in the deduced amino acid sequence which matches the amino-terminus of the mature $\beta_4$ protein previously determined in our laboratory except for two amino acids that were uncertain in the protein sequence (Kajiji et al., (1989), supra). The predicted extracytoplasmic domain of $\beta_4$ shows high homology to other integrin $\beta$-chains. This homology ends at the border of the extracytoplasmic region at the predicted transmembrane region. After this point, the $\beta_4$ sequence is completely divergent, with the exception of two conserved residues (WK) positioned at the end of the transmembrane region, which may, therefore, be essential for structure or function.

Figure 7A:
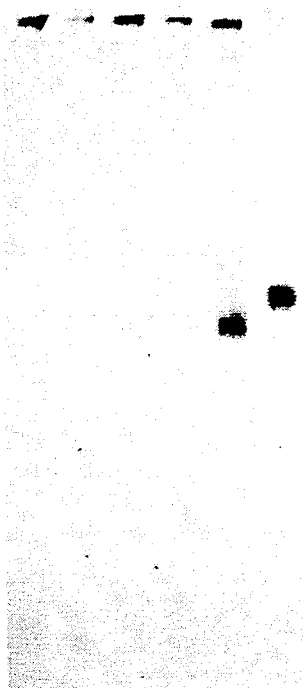
FIGS. 7A and 7B are photocopies of an autoradiogram of $\beta_4$ immunoprecipitated with antibodies selected with the lam 18.2.1 fusion protein.
Figure 7B:
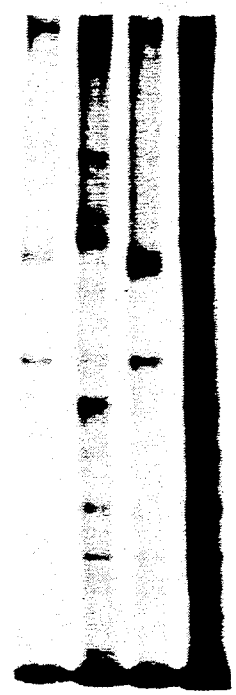

While $\beta_1$, $\beta_2$ and $\beta_3$ have a cytoplasmic tail of the same length (47 amino acids) with many identities or conserved substitutions, these sequences are entirely absent from $\beta_4$. Instead, $\beta_4$ contains a surprisingly large cytoplasmic domain comprised of more than 1000 residues. We have provided direct evidence that the putative cytoplasmic domain deduced from these cDNA clones is, in fact, part of the $\beta_4$ protein (FIGS. 7A and 7B).

While the extracellular portion of $\beta_4$ aligns with the other integrin $\beta$-chains, no significant homologies with other proteins were found for the $\beta_4$ cytoplasmic sequence by searching the Genbank database (Release 62) with the TFASTA program (Pearson and Lipman, 1988). However, dot-matrix analyses (COMPARE and DOTPLOT), revealed a repeat region in the cytoplasmic tail. A sequence of frequency matrix derived from this three-fold repeat (PROFILE) was used to search the NBRF data bank (PROFILESEARCH). Significant similarity was found with type III fibronectin repeats (Kornblihtt et al., 1985; Petersen et al., 1983).

A. Evidence for possible multiple forms of $\beta_4$ mRNAs.

Some of the cDNA clones were found to contain insertions in two locations: one in the 5'-untranslated region and the other in the coding region corresponding to the cytoplasmic tail.

Thirteen independent clones, covering the 5'-end of the $\beta_4$ cDNA were sequenced. Six of them had an insertion of 49 bp in the 5'-untranslated sequence after position 129, 9 bp upstream of the ATG initiation codon (FIG. 8A).

The second extra sequence was found in the cytoplasmic tail where in one out of the five clones analyzed there was an insertion of 70 amino acids precisely in frame between threonine 1369 and glutamic acid 1440, located after bp 4294 (FIGS. 8A and 8B).

These extra sequences raised the possibility that multiple forms of $\beta_4$ cDNA exist in carcinoma cells. In addition, $\beta_4$ cDNA from normal epithelial cells were recently reported (Suzuki and Naitoh, (1990) *EMBO* 9:757–763; Hogervorst et al., (1990) EMBO 9:765–770). One of these contains a 159 bp sequence in the cytoplasmic coding region that is not present in any of our clones located after bp 4744 (FIG. 8B).

In order to determine whether these sequences were actually present in cellular mRNAs, we amplified mRNAs from various cells using PCR. Oligonucleotide primers flanking the sites of insertion were synthesized (in one case, see FIG. 11A, an internal primer was used) as described in "Materials and Methods." (In FIG. 11A, solid lines represent the regions of the cDNAs being amplified. The boxes with vertical lines represent the potential inserts observed, and the box with diagonal lines represent the potential insert in the $\beta_4$ sequence reported by Hogervorst et al. (1990), supra; numbers to the left of each line are the size of the expected PCR product; numbers above each line are the nucleotide positions just preceding the insert based on the numbering scheme shown in FIGS. 8A and 8B; position and orientation of primers is shown by arrowheads; oligonucleotides 1+2 were used for insert 4,294 and 5+6 were used for insert 4,744.) PCRs using the primers flanking the 5'-region insert generated products in both FG and LoVo cDNAs, consistent with the two types of cDNA we found, i.e., with or without the 49 bp insert (248 bp and 200 bp, respectively; FIG. 11B, lanes 1,2). Of these, only the 200 bp band (i.e., without the insert) was obtained from placental mRNA (FIG. 11B, lane 3). Unexpectedly, one band of 260 bp was seen in carcinoma cells, and two bands at 255 bp and 180 bp were seen in placental amplification products, suggesting the possibility of additional insertions in this region. The low intensity of the bands obtained from placental cDNA for the amplification of this region may be explained by low representation of 5' mRNA sequences due to degradation during mRNA extraction from tissue.

Using oligonucleotide primers specific to the region containing the insert at bp 4294 (FIG. 11B, lanes 4-6), a band of 255 bp was amplified from both LoVo and FG cDNAs but not from placenta, suggesting that mRNA containing this insert is expressed in carcinoma but not in normal cells.

PCR amplifications with primers flanking the insert at bp 4744 (Hogervorst et al., (1990) supra; FIG. 11B, lanes 7-9) suggest that mRNAs, both with and without this insert, are present in placental tissue and that the form containing the insert is prevalent. Instead, LoVo and FG carcinoma cell mRNA produce only PCR bands corresponding to the insert-minus form. These results have been extended to a variety of cultured cell lines and a few normal tissues, as shown in Table 5, below:

TABLE 5

| DISTRIBUTION OF $\beta_4$ VARIANTS | | |
|---|---|---|
| Insert at Base Pair 4294 | Insert at Base Pair 4744 | No Insert |
| FG-2 | + | — — | + |
| Panc I | — — | — — | + |
| Hela | — — | — — | + |
| Jar | + | — — | + |
| CoLo 396 | + | — — | + |
| LoVo | — — | — — | + |
| UCLA P3 | — — | — — | + |
| A431 | — — | — — | + |
| M21 | — — | — — | — — |
| Placenta | — — | + | + |
| Cervix | + | + | + |

These results suggest that multiple alternatively spliced forms of $\beta_4$ exist, and that they are distributed in a differential manner in normal as well as transformed epithelial cells.

The $\beta_4$ sequences obtained from carcinoma cells contain several differences compared to the $\beta_4$ cDNAs isolated from normal epithelial cells (Hogervorst et al., (1990) supra; Suzuki and Naitoh, (1990), supra). Clones encoding two versions of the cytoplasmic tail of $\beta_4$ were discovered. Although one of these is identical to that reported by Suzuki and Naitoh (1990), supra, the other contains an insertion of 70 amino acids after threonine 1369. Both sequences disclosed herein are different from that reported by Hogervorst et al. (1990), supra, which contains an insertion of 53 amino acids after histidine 1519. Another distinctive feature of the $\beta_4$ cDNAs disclosed herein is an insertion of 49 bp in the 5' untranslated region, 9 bp upstream the ATG initiator codon. This sequence was found in approximately 50% of the clones we analyzed. Some or all of these insertions may be due to alternative exon splicing during the maturation of mRNA transcripts. (Such mechanisms have been described in other mRNAs including the integrin subunits $\beta_3$ (van Kuppevelt et al., 1989) and PS2 $\alpha$ (Brown et al., (1989) Cell 59:185-195). Consistent with the possibility of alternative splicing, PCR amplification products of the expected size were detected using primers located either within or adjacent to the insertions. That mature cytoplasmic mRNA, rather than immature nuclear transcripts, acted as templates in these PCR reactions is suggested by the fact that independent poly (A)+ RNA preparations yielded identical results, and that the relative ratio of the various forms remained constant within, and was characteristic of, a given cell type. For instance, the 4744 insert was detectable in placenta but not in carcinoma cells, while the 4294 insert had the opposite pattern (FIG. 11B).

B. CELLULAR DISTRIBUTION OF $\alpha_6\beta_4$

The long cytoplasmic tail of $\beta_4$ is suggestive of unique intracellular interactions with cytoskeletal components. To gain some information on this possibility, the cellular distribution of $\alpha_6\beta_4$ with respect to adhesion plaques was examined by immunofluorescence studies. FG carcinoma cells were plated on Matrigel-coated glass, fixed, permeabilized, and stained by specific antibodies after 2 d of culture. The majority of the cells in these cultures had a typical epithelial appearance, forming clusters of 3-20 cells with epithelioid geometry, as evidenced by phase-contrast microscopy (FIGS. 12A-12G, FIG. 5A). That these cells form adhesion plaques was shown by staining with antibodies to vinculin and talin, which can be visualized as spots on the external edges of spread cells in the periphery of the clusters FIGS. 12A, 12C and 12E (phase contrast, plane of focus at the basal surface of cells)). Actin, specifically stained by fluorescent phalloidin, was also observed on the outer edges of spread cells in a pattern of spikes, and on the inside of these cells in small patches (FIG. 12D). However, no clearly recognizable actin stress fibers were seen.

In cells stained simultaneously for both talin and $\beta_4$ (FIG. 12G) the talin staining on the outer edges was often juxtaposed to that of $\beta_4$, but was not overlapping. In parts of the basal surface interior to the edge of the cells, talin was not detectable, while $\beta_4$ was visible and appeared to be arranged in small patches and streaks (FIG. 12F) (anti-talin antibodies) and FIG. 12G (simultaneous staining with anti-$\beta_4$ antibodies), areas of interest are indicated as follows: wavy arrows, areas internal to the edges were stained by anti-$\beta_4$ antibodies but not anti-talin antibodies; straight arrows, areas on the edges of the peripheral, spread cells where talin and $\beta_4$ staining are juxtaposed but not overlapping; arrowheads, areas where talin and $\beta_4$ staining were observed by careful focussing to be distinct.; bar, 10 μm). Cells double-stained with both anti-vinculin (mouse monoclonal) and anti-$\alpha_6$ cytoplasmic tail (rabbit antibodies) gave very similar patterns to the cells double stained for talin and $\beta_4$. These results suggest that the cellular distribution of $\alpha_6\beta_4$ is distinct from that of adhesion plaques.

EXAMPLE 6

THERAPEUTIC TREATMENT OF HPC

Patients determined to have HPC are treated with monoclonal antibodies reactive with HPC cells and conjugated with a toxin such as ricin, or any cytotoxic drug. The monoclonal antibody conjugates are administered (intravenously, intramuscularly, intra peritoneally, or the like, in a physiologically acceptable carrier solution, such as phosphate buffered saline. The dosage is determined by the body weight of the host, it preferably being in the range of about 0.1 mg/kg to about 40 mg/kg body weight, and usually about 1 mg/kg to about 10 mg/kg of host body weight. Alternatively, the dosage is established by evaluating the extent of the tumor as by quantitatively standardized ELISA, radioimaging or other methods. Treatment is repeated at intervals as necessary, to effect enhancement of the host's ability to recover from the injection.

EXAMPLE 7

IMAGING OF HPC TUMOR

Monoclonal antibodies reactive with HPC cells are utilized to determine the location and extent of HPC by methods well-known in the art, for example, Larson et al. (1983) *J. Clinical Investigation* 72:2101, which is incorporated by reference. Monoclonal antibodies are preferably radiolabeled by radioiodination or by other radiolabeling techniques well known in the art, such as chelation using a chelating agent such as diethylene triaminepenta-acetic acid (DTPA); or are otherwise labeled, such as with agents having paramagnetic properties, with chemiluminescent substrates, or with components of an enzymatic reaction. The radiolabeled monoclonal antibodies are purified and formulated for pharmaceutical use. A solution of the labeled monoclonal antibodies in a carrier, for example in phosphate buffered saline, is injected intravenously into a host. The appropriate dose is in the range of about 100 mg to 50 mg. Time is permitted for the antibodies to migrate to regions of the body having concentrations of cells with antigenic determinants reactive therewith. Concentrations of radioisotopes in certain tissues are determined or may be mapped either by techniques of whole body imaging which are well-known in the art, (See, for example, Rainsbury et al. (1983) *Lancet* Oct. 22, 934 (1983)) which is incorporated by reference, or by evaluating biopsied tissue or extracted body fluid using a scintillation counter. Where nonradioactive labels are used, other appropriate monitoring means are employed, such as a detector of nuclear magnetic resonance or a spectrophotometer. Areas of high radiation levels are indicative of the presence of cells such as HPC, having the cell surface markers of the present invention.

EXAMPLE 8

DIAGNOSIS OF PATHOLOGICAL CONDITIONS

The monoclonal antibodies of the present invention have applications beyond diagnosis of HPC tumor. Due to the putative role of $\alpha_6\beta_4$ in cell adhesion, one would expect to use monoclonal antibodies specific for $\alpha_6\beta_4$ to identify abnormal conditions. For example, in normal cervical tissues, $\alpha_6\beta_4$ is expressed by epithelial cells at the interface with the basement membrane. Immunostaining of $\alpha_6\beta_4$ indicates a sharp line of demarcation at the epithelial/basement membrane interface. Thus, normal cervical tissue has an orderly arrangement of $\alpha_6\beta_4$ at the epithelial/basement membrane interface, which is consistent with the role of $\alpha_6\beta_4$ as a cell adhesion protein. In pathological cervical tissue, one would expect to see an irregular staining pattern thereby enabling early diagnosis and treatment of life threatening illness. Similarly, the present invention makes possible the early detection of pathological conditions in other cells which exhibit a regular, ordered distribution of $\alpha_6\beta_4$. Such tissues would include, but are not limited to, the skin, the digestive tract, and the mammary glands. Thus, skin diseases such as various cancerous and non-cancerous disorders (e.g. blistering conditions and psoriasis) can be detected using the Mabs present invention. Similarly, diseases affecting the epithelia of the digestive tract and the mammary glands could also be detected by determining irregularities from the normally-ordered staining patterns of healthy tissues.

Alternatively, it is known that in some tissues (e.g. pancreas) normal cells typically do not bear the receptor $\alpha_6\beta_4$. Without wishing to be bound by this theory, it is postulated that $\alpha_6\beta_4$ is an important adhesion protein in metastasizing cancer cells enabling these cells to attach to various basement membranes and proliferate. Thus, the monoclonal antibodies of the present invention are useful in detecting the abnormal presence of $\alpha_6\beta_4$ on cells that normally do not express it. The monoclonal antibodies of the present invention are also useful in therapeutic applications in which one would conjugate the antibody to a toxin or radiolabel, determine the range at which abnormal cells carrying the $\alpha_6\beta_4$ receptor were maximally targeted and killed and normal cells were minimally destroyed, and administer that appropriate amount of Mab.

Alternatively, one can use the present invention to do in situ hybridization and PCR. (For example, one could perform in situ reverse transcription followed by PCR amplification; if desired amplification can be performed semi-quantitatively to determine the amount of $\alpha_6\beta_4$ mRNA present in a given cell.) Thus, nucleic acid probes based on cDNA structures reported herein (including oligonucleotides, etc.) have useful, diagnostic applications as well.

The foregoing examples provide specific embodiments of the present invention, other embodiments being readily within the skill in the art. Thus, the scope of the present invention is defined by the following claims without limitation to the foregoing examples.

We claim:

1. A method of diagnosing the presence of abnormal epithelial tissue in vitro, said method comprising:
   (a) contacting a tissue sample with the monoclonal antibody designated S3-41, having A.T.C.C. Accession No. HB 9318, which immunologically binds to the $\alpha_6\beta_4$ cell surface marker protein;
   (b) locating said bound antibody in said tissue sample; and
   (c) determining whether said location of said bound antibody indicates the presence of abnormal epithelium in said tissue sample.

2. The method of claim 1 wherein said monoclonal antibody is located using immunofluorescence.

* * * * *